United States Patent
Duindam et al.

(10) Patent No.: US 11,779,396 B2
(45) Date of Patent: Oct. 10, 2023

(54) SYSTEMS AND METHODS FOR REGISTERING ELONGATE DEVICES TO THREE DIMENSIONAL IMAGES IN IMAGE-GUIDED PROCEDURES

(71) Applicant: INTUITIVE SURGICAL OPERATIONS, INC., Sunnyvale, CA (US)

(72) Inventors: Vincent Duindam, San Francisco, CA (US); Federico Barbagli, San Francisco, CA (US); Timothy D. Soper, San Jose, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 377 days.

(21) Appl. No.: 16/473,439

(22) PCT Filed: Jan. 9, 2018

(86) PCT No.: PCT/US2018/012969
§ 371 (c)(1),
(2) Date: Jun. 25, 2019

(87) PCT Pub. No.: WO2018/129532
PCT Pub. Date: Jul. 12, 2018

(65) Prior Publication Data
US 2019/0320878 A1     Oct. 24, 2019

Related U.S. Application Data

(60) Provisional application No. 62/444,018, filed on Jan. 9, 2017.

(51) Int. Cl.
*G06T 7/11*     (2017.01)
*G06T 7/30*     (2017.01)
(Continued)

(52) U.S. Cl.
CPC .............. *A61B 34/10* (2016.02); *A61B 1/009* (2022.02); *A61B 1/000094* (2022.02);
(Continued)

(58) Field of Classification Search
CPC ....... G06T 7/0012; G06T 7/0014; G06T 7/11; G06T 7/10; G06T 7/30; G06T 7/32;
(Continued)

(56) References Cited

U.S. PATENT DOCUMENTS 6,380,732 B1     4/2002    Gilboa et al.
6,389,187 B1     5/2002    Greenaway et al.
(Continued)

FOREIGN PATENT DOCUMENTS

CN          101214142 A       7/2008
WO     WO-2011128797 A1      10/2011
(Continued)

OTHER PUBLICATIONS

International Search Report and Written Opinion for Application No. PCT/US2018/012969, dated Jun. 20, 2018, 12 pages.
(Continued)

*Primary Examiner* — Carolyn A Pehlke
(74) *Attorney, Agent, or Firm* — HAYNES AND BOONE, LLP

(57) ABSTRACT

Methods for using registered real-time images and prior-time anatomic images during an image-guided procedure are provided herein. An exemplary method includes obtaining a three-dimensional image of a patient anatomy and a portion of a medical instrument disposed therein. The three-dimensional image includes image information characterizing a shape of the portion of the medical instrument. A processing device segments the portion of the medical instrument from the three-dimensional image. Shape data is obtained from the portion of the medical instrument while the portion is
(Continued)

positioned within the patient anatomy, and the processing device registers the segmented shape of the portion of the medical instrument with the shape data from the portion of the medical instrument.

20 Claims, 12 Drawing Sheets

(51) Int. Cl.
<table>
<tr><td>A61B 6/03</td><td>(2006.01)</td></tr>
<tr><td>A61B 6/00</td><td>(2006.01)</td></tr>
<tr><td>A61B 34/10</td><td>(2016.01)</td></tr>
<tr><td>A61B 1/00</td><td>(2006.01)</td></tr>
<tr><td>A61B 1/005</td><td>(2006.01)</td></tr>
<tr><td>A61B 10/02</td><td>(2006.01)</td></tr>
</table>

(52) U.S. Cl.
CPC .............. *A61B 6/032* (2013.01); *A61B 6/466* (2013.01); *G06T 7/11* (2017.01); *G06T 7/30* (2017.01); *A61B 1/005* (2013.01); *A61B 10/02* (2013.01)

(58) Field of Classification Search
CPC .......... G06T 7/33; G06T 7/337; G06T 7/344; A61B 90/37; A61B 2090/364; A61B 2090/365; A61B 2090/366; A61B 2034/2046; A61B 2034/2061; A61B 2034/2065; A61B 2034/2074; A61B 34/20; A61B 34/25; A61B 6/504
See application file for complete search history.

(56) References Cited

U.S. PATENT DOCUMENTS

<table>
<tr><td>7,316,681 B2</td><td>1/2008</td><td>Madhani et al.</td></tr>
<tr><td>7,772,541 B2</td><td>8/2010</td><td>Froggatt et al.</td></tr>
<tr><td>8,611,985 B2 *</td><td>12/2013</td><td>Lavallee ............ A61B 17/3478<br>382/128</td></tr>
<tr><td>8,900,131 B2</td><td>12/2014</td><td>Chopra et al.</td></tr>
<tr><td>9,259,274 B2</td><td>2/2016</td><td>Prisco et al.</td></tr>
<tr><td>9,452,276 B2</td><td>9/2016</td><td>Duindam et al.</td></tr>
<tr><td>10,762,380 B2 *</td><td>9/2020</td><td>Ekin ..................... G06T 7/73</td></tr>
<tr><td>2002/0188174 A1 *</td><td>12/2002</td><td>Aizawa ................. A61B 5/064<br>600/109</td></tr>
<tr><td>2006/0013523 A1</td><td>1/2006</td><td>Childlers et al.</td></tr>
<tr><td>2007/0055128 A1</td><td>3/2007</td><td>Glossop et al.</td></tr>
<tr><td>2007/0100223 A1 *</td><td>5/2007</td><td>Liao ........................ G06T 7/30<br>600/407</td></tr>
<tr><td>2007/0167714 A1</td><td>7/2007</td><td>Kiraly et al.</td></tr>
<tr><td>2013/0195338 A1</td><td>8/2013</td><td>Xu et al.</td></tr>
<tr><td>2013/0338477 A1 *</td><td>12/2013</td><td>Glossop ............. A61B 10/0241<br>600/407</td></tr>
<tr><td>2014/0114180 A1 *</td><td>4/2014</td><td>Jain ....................... A61B 6/481<br>600/424</td></tr>
<tr><td>2014/0276937 A1 *</td><td>9/2014</td><td>Wong .................... A61B 34/37<br>606/130</td></tr>
<tr><td>2014/0343416 A1 *</td><td>11/2014</td><td>Panescu ................ A61B 34/30<br>600/431</td></tr>
<tr><td>2015/0254526 A1 *</td><td>9/2015</td><td>Denissen .................. G06T 7/50<br>382/128</td></tr>
<tr><td>2016/0101263 A1 *</td><td>4/2016</td><td>Blumenkranz ...... A61B 1/0051<br>600/117</td></tr>
<tr><td>2017/0265840 A1 *</td><td>9/2017</td><td>Bharat ................... A61B 5/061</td></tr>
<tr><td>2018/0008222 A1 *</td><td>1/2018</td><td>Chen ..................... A61B 6/504</td></tr>
<tr><td>2018/0056040 A1</td><td>3/2018</td><td>Fenech et al.</td></tr>
<tr><td>2018/0235709 A1</td><td>8/2018</td><td>Donhowe et al.</td></tr>
<tr><td>2018/0240237 A1</td><td>8/2018</td><td>Donhowe et al.</td></tr>
</table>

FOREIGN PATENT DOCUMENTS

<table>
<tr><td>WO</td><td>WO-2013001388 A1</td><td>1/2013</td><td></td></tr>
<tr><td>WO</td><td>WO-2015023665 A1 *</td><td>2/2015</td><td>............ A61B 5/066</td></tr>
<tr><td>WO</td><td>WO-2016018646 A1</td><td>2/2016</td><td></td></tr>
<tr><td>WO</td><td>WO-2016025465 A1</td><td>2/2016</td><td></td></tr>
<tr><td>WO</td><td>WO-2016191298 A1</td><td>12/2016</td><td></td></tr>
<tr><td>WO</td><td>WO-2019018736 A2</td><td>1/2019</td><td></td></tr>
</table>

OTHER PUBLICATIONS

International Preliminary Report on Patentability for Application No. PCT/US2018/012969, dated Jul. 18, 2019, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

SYSTEMS AND METHODS FOR REGISTERING ELONGATE DEVICES TO THREE DIMENSIONAL IMAGES IN IMAGE-GUIDED PROCEDURES

CROSS-REFERENCE TO RELATED APPLICATIONS

This patent application is the U.S. national phase of International Application No. PCT/US2018/012969, filed Jan. 9, 2018, which designated the U.S. and claims priority to and benefit of the filing date of U.S. Provisional Patent Application No. 62/444,018, entitled "Systems and Methods for Registering Elongate Devices to Three-Dimensional Images in Image-Guided Procedures," filed Jan. 9, 2017, all of which are hereby incorporated by reference in their entirety.

FIELD

The present disclosure is directed to systems and methods for conducting an image-guided procedure, and more particularly to systems and methods for using registered real-time images and prior-time anatomic images during an image-guided procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physicians may insert minimally invasive medical instruments (including surgical, diagnostic, therapeutic, or biopsy instruments) to reach a target tissue location. To assist with reaching the target tissue location, the location and movement of the medical instruments may be correlated with preoperative images of the patient anatomy. With the image-guided instruments correlated to the images, the images may be used to help the instruments navigate through natural or surgically created passageways in anatomic systems such as the lungs, the colon, the intestines, the kidneys, the heart, the circulatory system, or the like. While the preoperative images are helpful, they are static representations often taken well before a procedure.

Accordingly, it would be advantageous to provide registration of an instrument with imaging modalities which capture images of patent anatomy during a procedure, to provide enhanced navigation information for performing image-guided procedures.

SUMMARY

The embodiments of the invention are summarized by the claims that follow the description.

In one embodiment, a method is performed by a computing system. The method includes obtaining a three-dimensional image of a patient anatomy and a portion of a medical instrument disposed therein. The three-dimensional image includes image information characterizing a shape of the portion of the medical instrument. A processing device segments the portion of the medical instrument from the three-dimensional image. Shape data is obtained from the portion of the medical instrument while the portion is positioned within the patient anatomy, and the processing device registers the segmented shape of the portion of the medical instrument with the shape data from the portion of the medical instrument. Other embodiments of this aspect include corresponding computer systems, apparatus, and computer programs recorded on one or more non-transitory computer storage mediums, each configured to perform the actions of the methods.

In another embodiment, a medical system comprises a medical instrument comprising a shape sensor, a tracking subsystem configured to receive shape data from the shape sensor, and a processor coupled to the medical instrument and the tracking subsystem. The processor is configured to receive image data of a patient anatomy that has the medical instrument disposed therein, such that the image data is in an image reference frame. The processor is further configured to: segment a portion of the image data corresponding to the medical instrument; obtain the shape data from the medical instrument that is in an instrument reference frame; and register the instrument reference frame to the image reference frame by comparing the shape data to the portion of the image data corresponding to the medical instrument.

In another embodiment, a method is performed by a computing system. The method includes obtaining imaging data of patient anatomy while a medical instrument is disposed within the patient anatomy. The imaging data includes a plurality of images and is in an image reference frame. Shape data is obtained from the medical instrument while the medical instrument is disposed within the patient anatomy. The shape data includes a plurality of subsets and is in an instrument reference frame. A subset of the plurality of subsets of shape data is matched to an image of the plurality of images, and the instrument reference frame is registered to the image reference frame based on comparing the matched subset of the plurality of subsets of shape data to the image of the plurality of images. Other embodiments of this aspect include corresponding computer systems, apparatus, and computer programs recorded on one or more non-transitory computer storage mediums, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 2A:
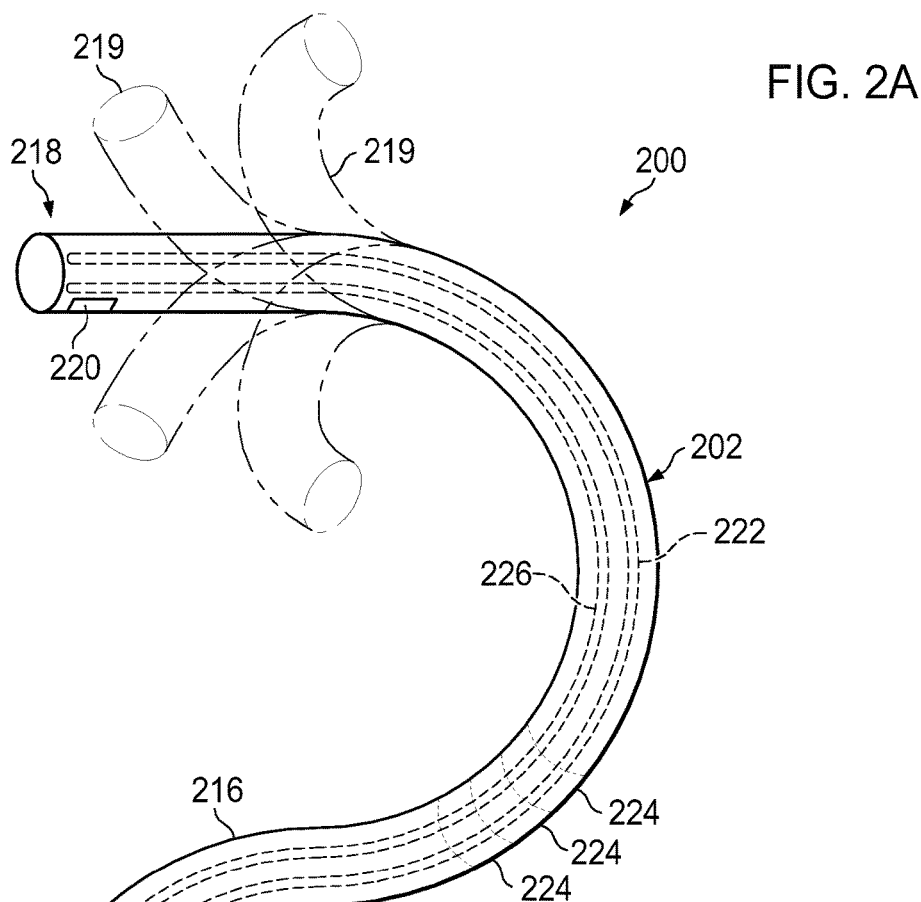
FIG. 2A illustrates a medical instrument system utilizing aspects of the present disclosure.
Figure 2B:
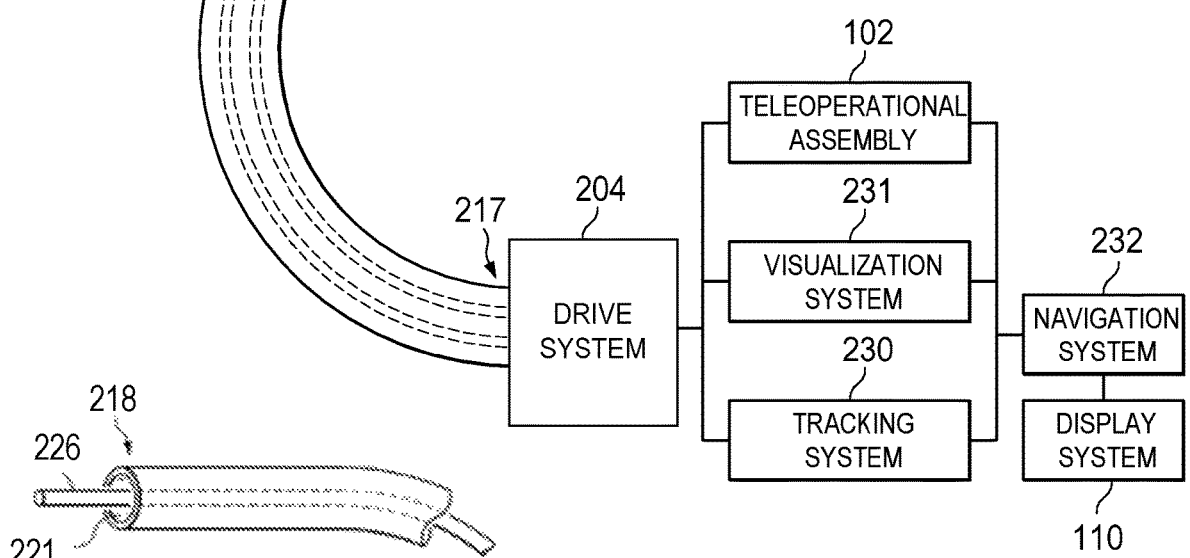
FIG. 2B illustrates a distal end of the medical instrument system of FIG. 2A with an extended medical tool, in accordance with embodiments of the present disclosure.
Figure 3A:
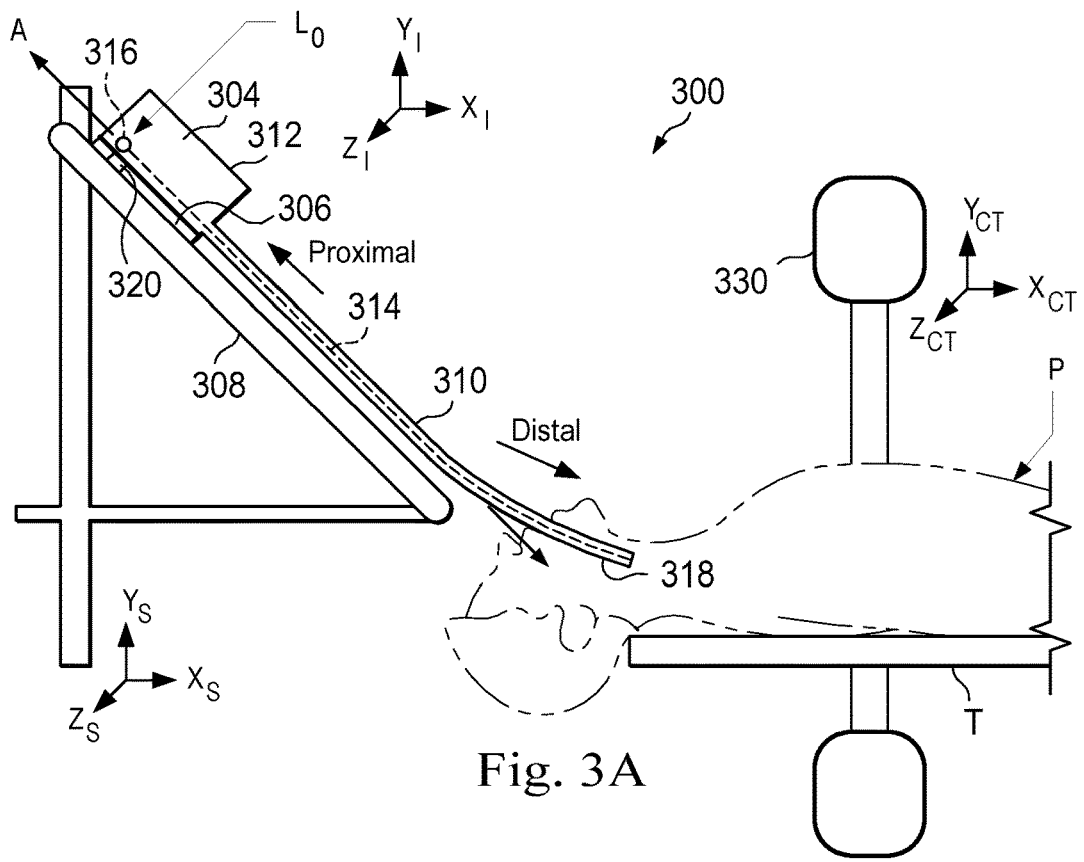
FIGS. 3A and 3B are simplified diagrams of side views of a patient coordinate space including a medical instrument mounted on an insertion assembly according to some embodiments.
Figure 3B:
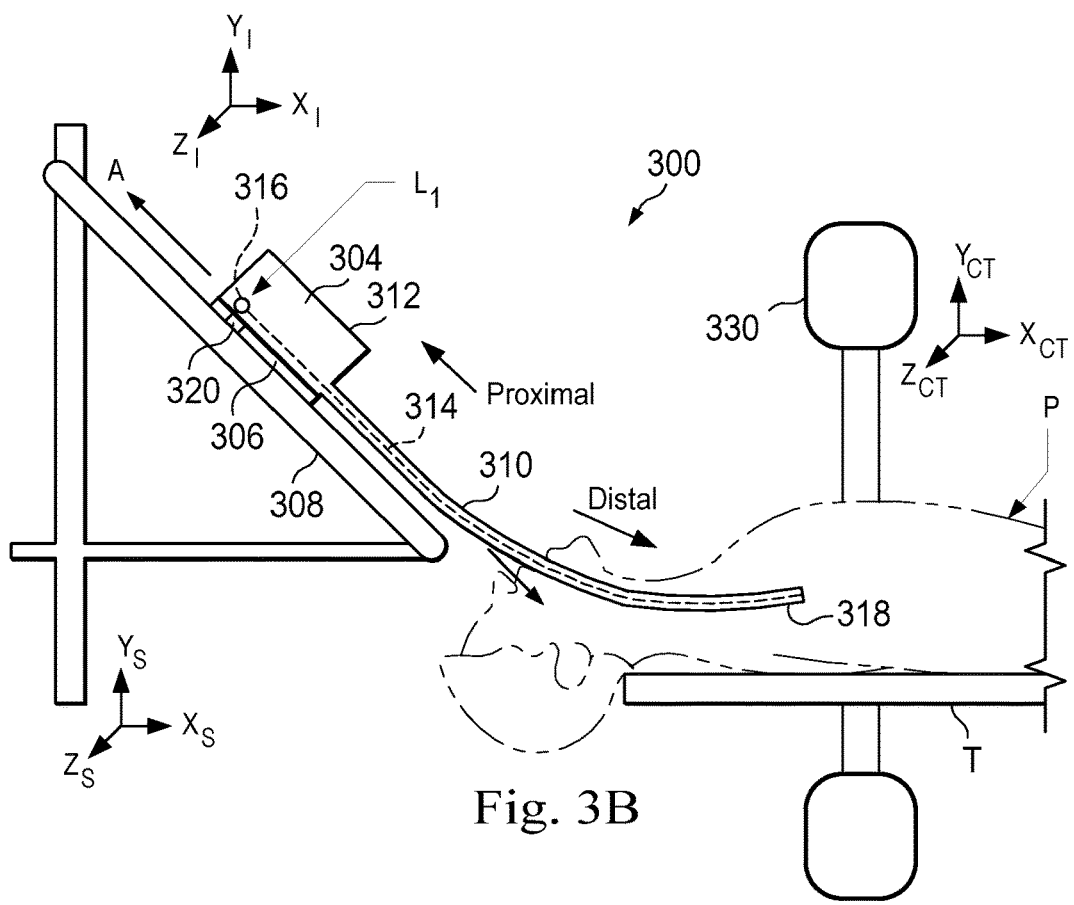
Figure 4A:
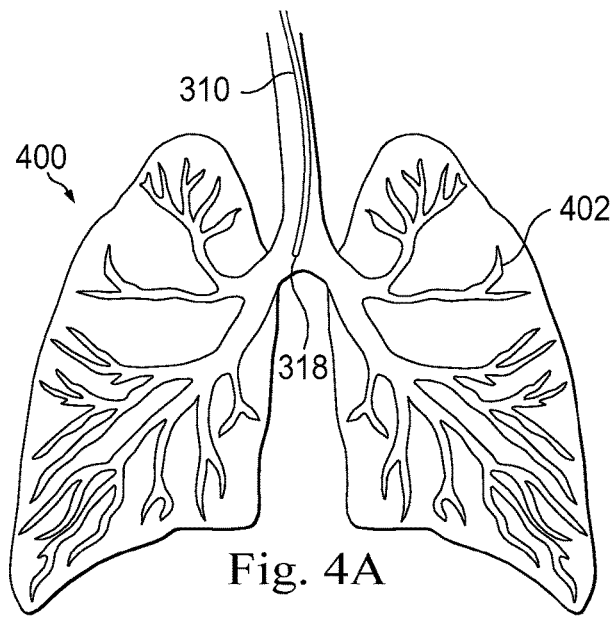
Figure 4B:
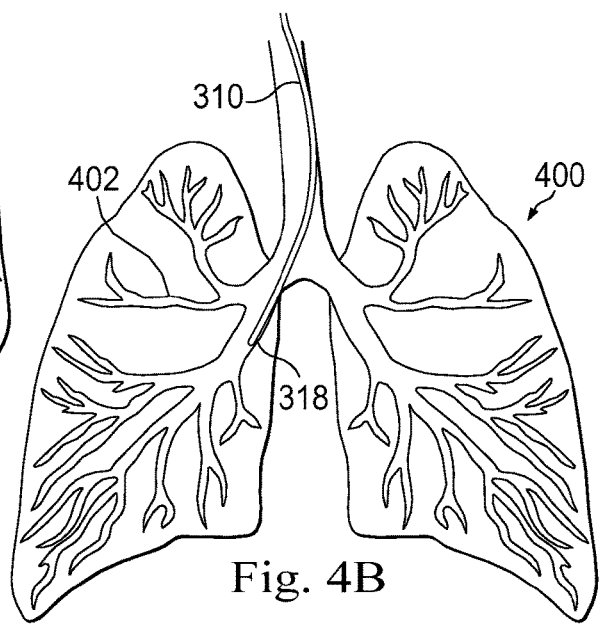
Figure 4C:
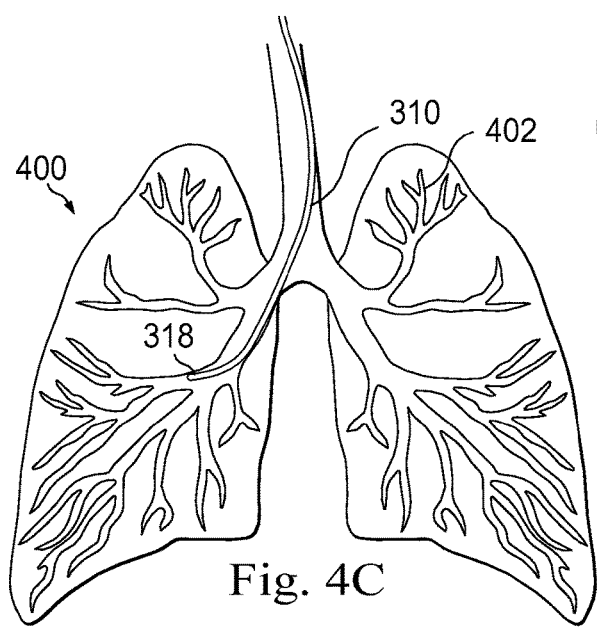
Figure 4D:
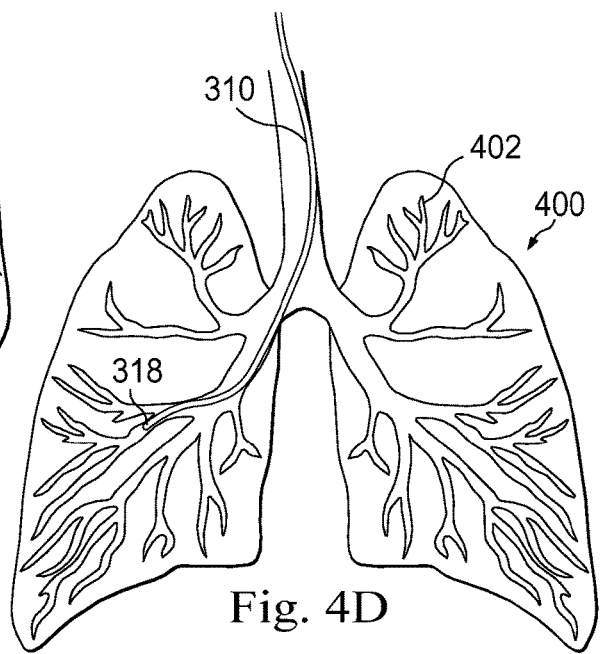

FIGS. 4A, 4B, 4C, and 4D illustrate the distal end of the medical robotic system of FIGS. 2, 3A, and 3B, during insertion within a human lung.

Figure 5:
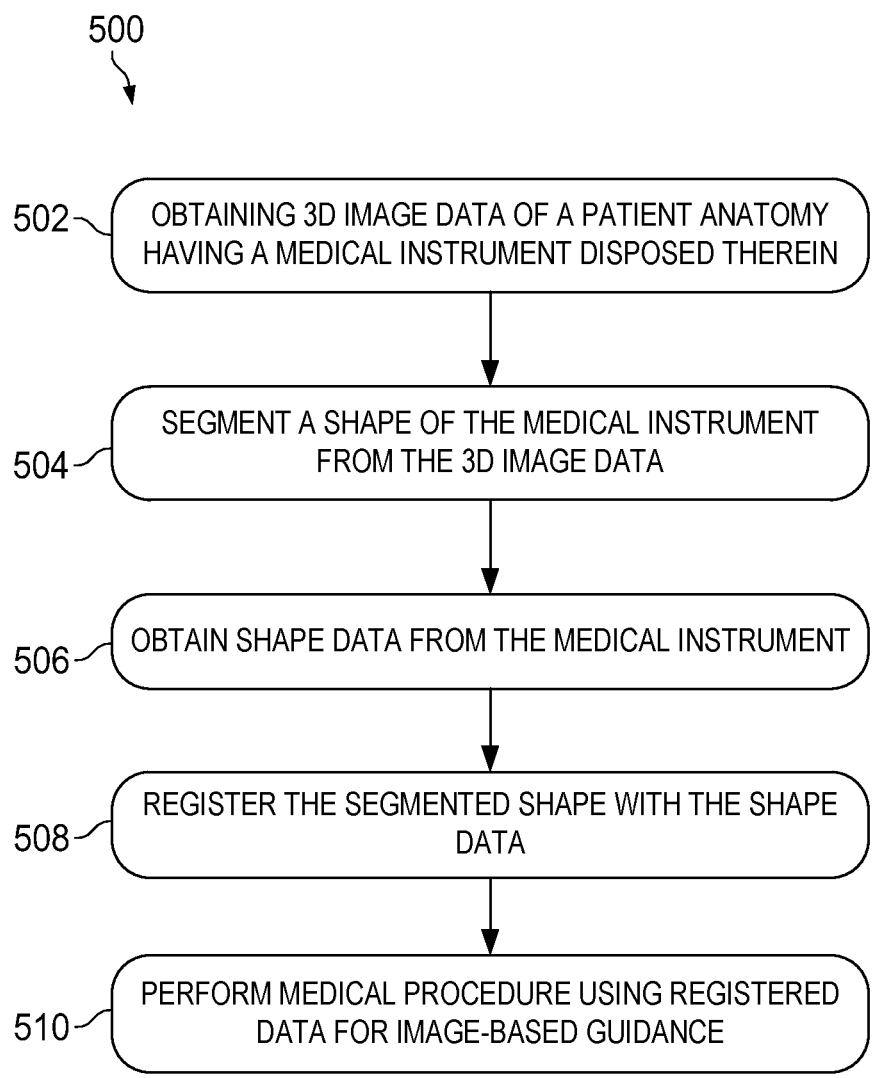

FIG. 5 illustrates a flowchart of an image-guided medical procedure according to an embodiment of the present disclosure.

Figure 6A:
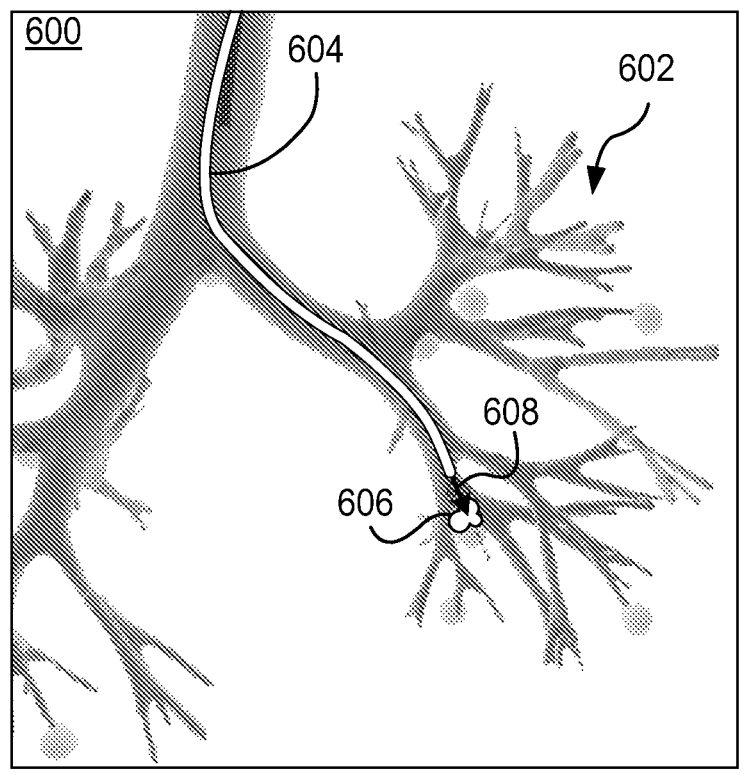

FIG. 6A illustrates an exemplary a filtered three-dimensional image including image information associated with bronchial passageways and a medical instrument, according to aspects of the present disclosure.

Figure 6B:
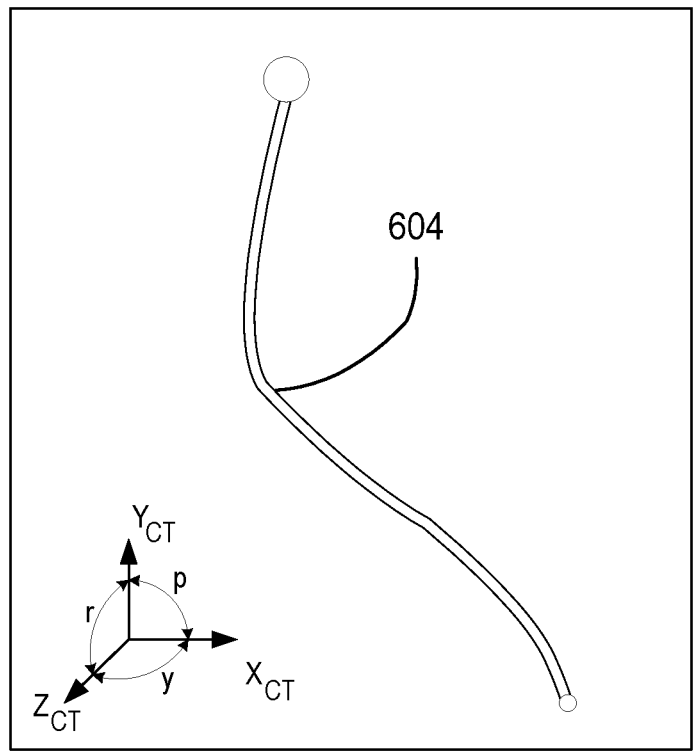

FIG. 6B illustrates a segmented model of the medical instrument of FIG. 6A, according to embodiments of the present disclosure.

Figure 7A:
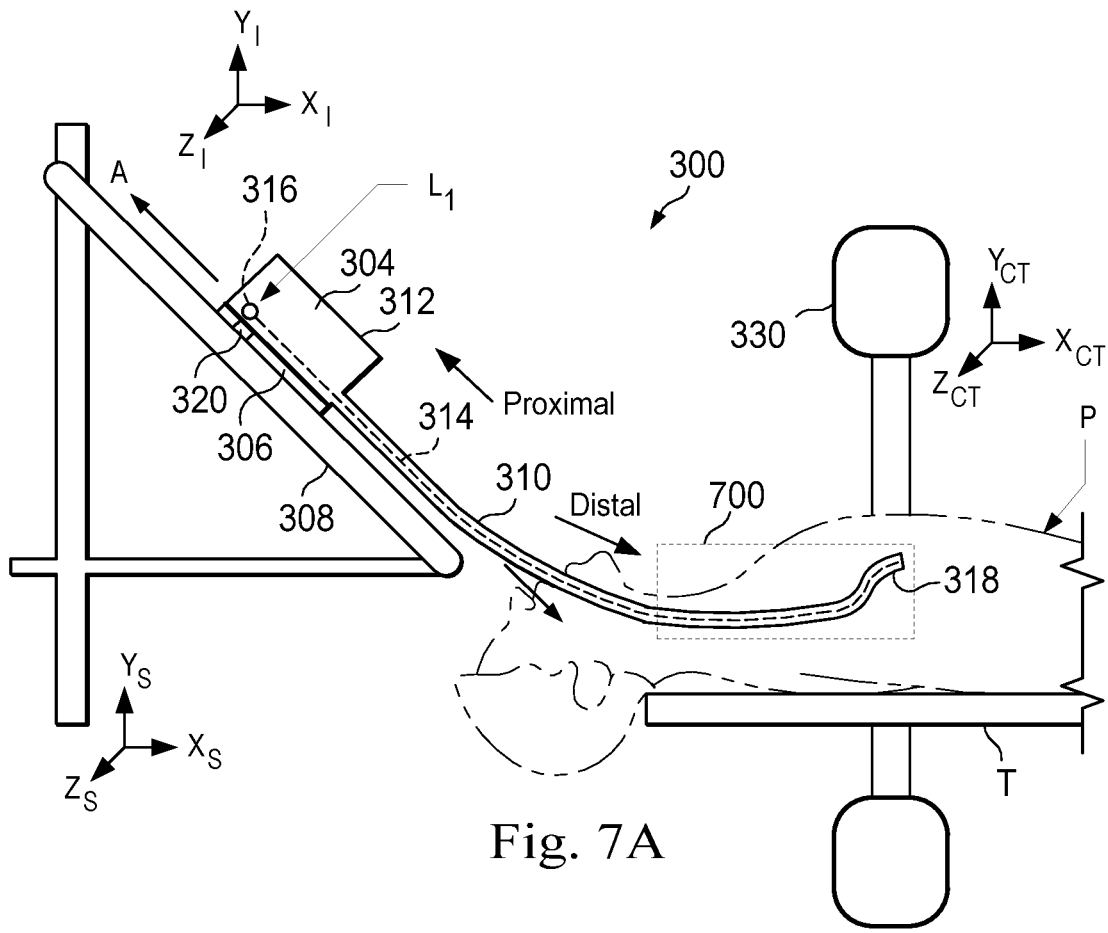

FIG. 7A is another side view of a surgical coordinate space including a medical instrument and a three-dimensional imaging system as seen in FIGS. 3A and 3B, according to aspects of the present disclosure.

Figure 7B:
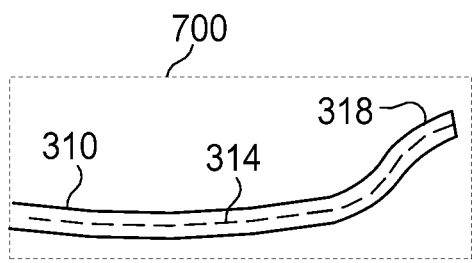

FIG. 7B illustrates a detailed view of a distal portion of the medical instrument shown in FIG. 7A.

Figure 7C:
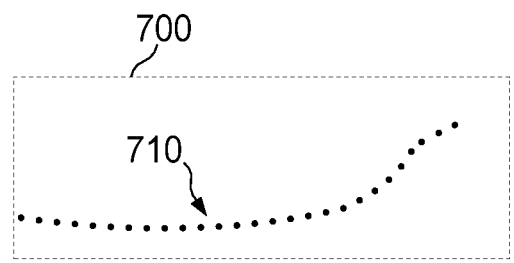

FIG. 7C illustrates shape data captured using the catheter medical instrument shown in FIGS. 7A and 7B, according to aspects of the present disclosure.

Figure 8:
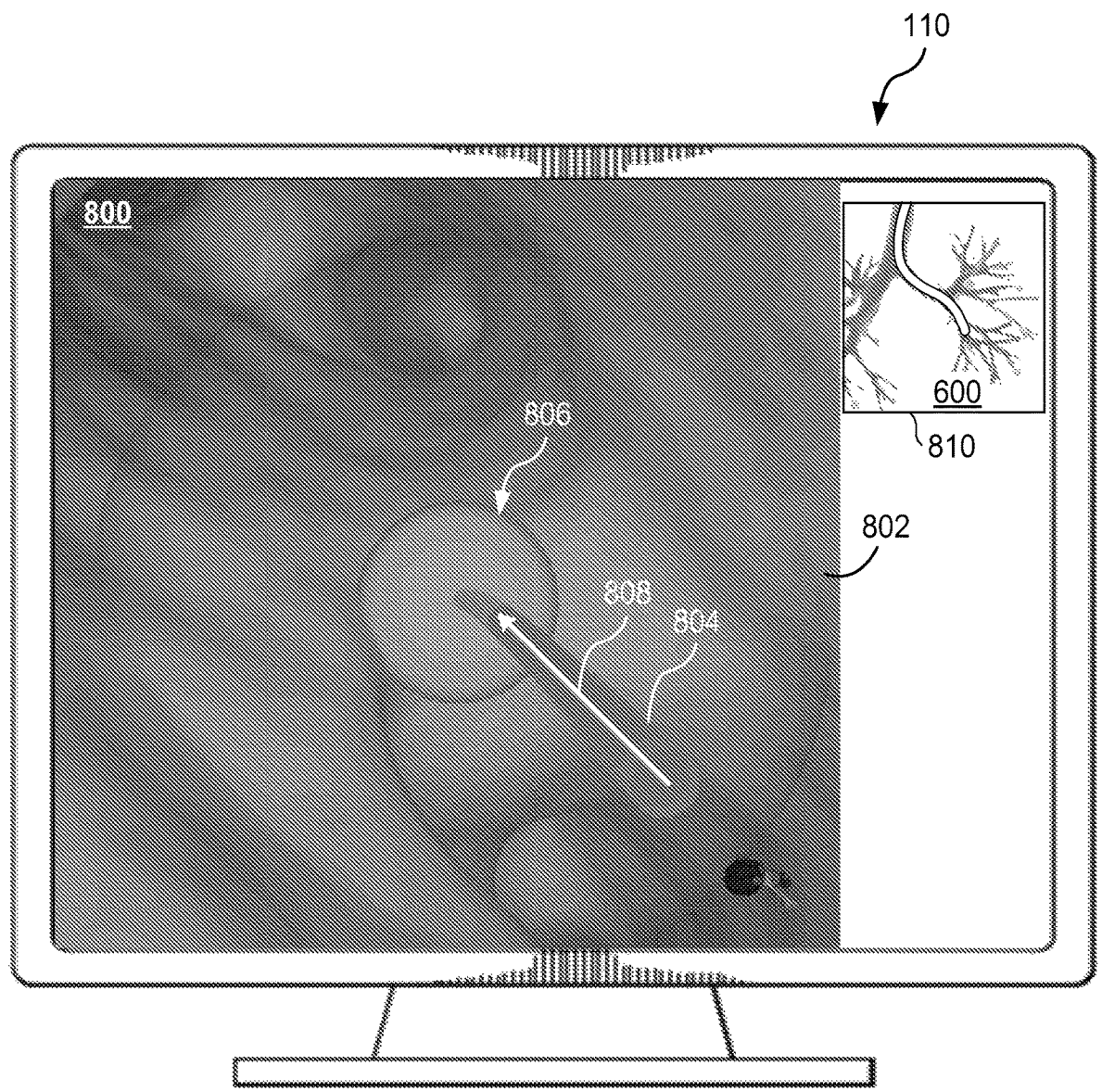

FIG. 8 illustrates an internal perspective of the three-dimensional image that is registered with a medical instrument in a common reference frame, according to aspects of the present disclosure.

Figure 9:
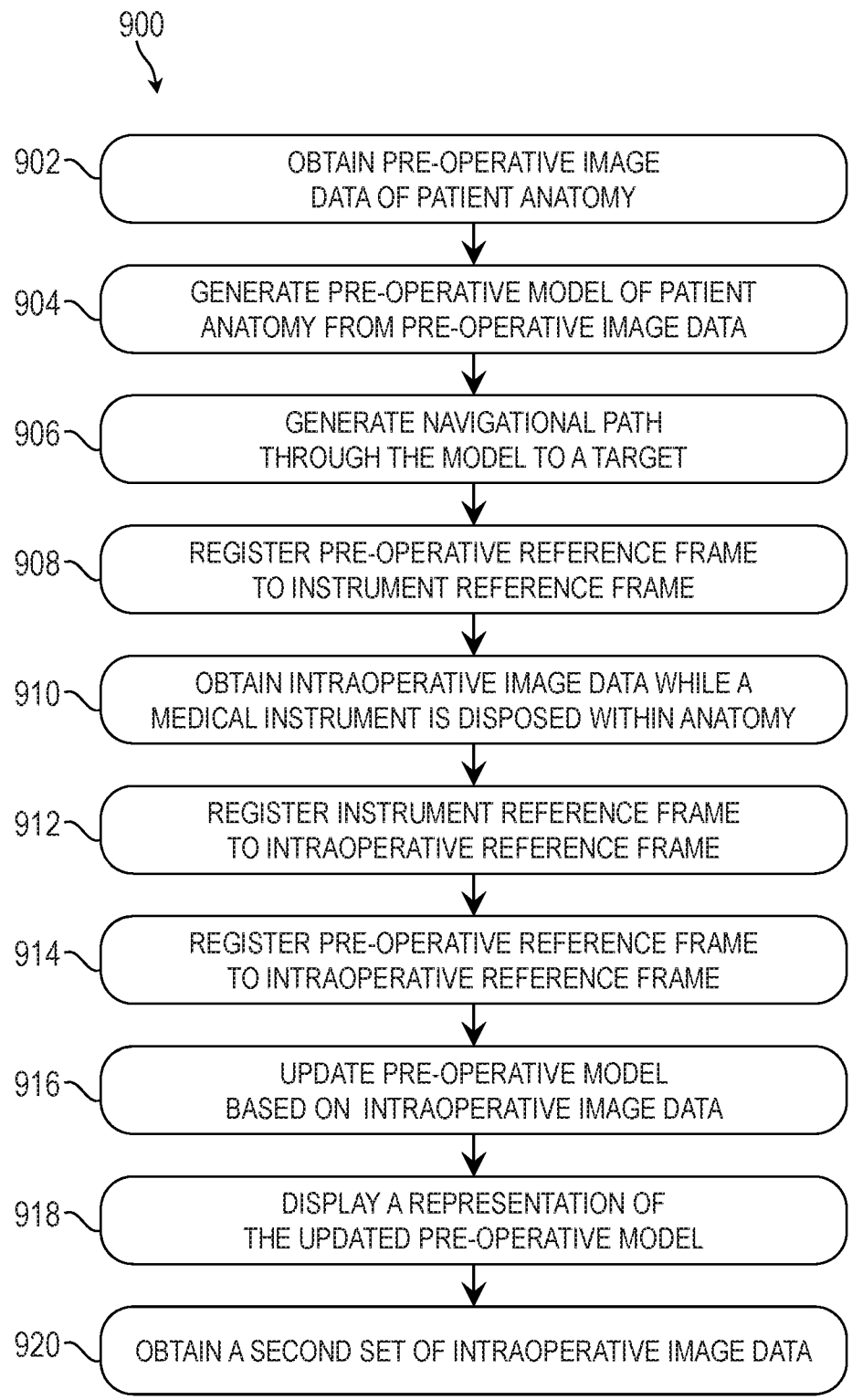

FIG. 9 illustrates a flowchart of a method for performing image guided surgery according to some embodiments of the present disclosure.

Figure 10A:
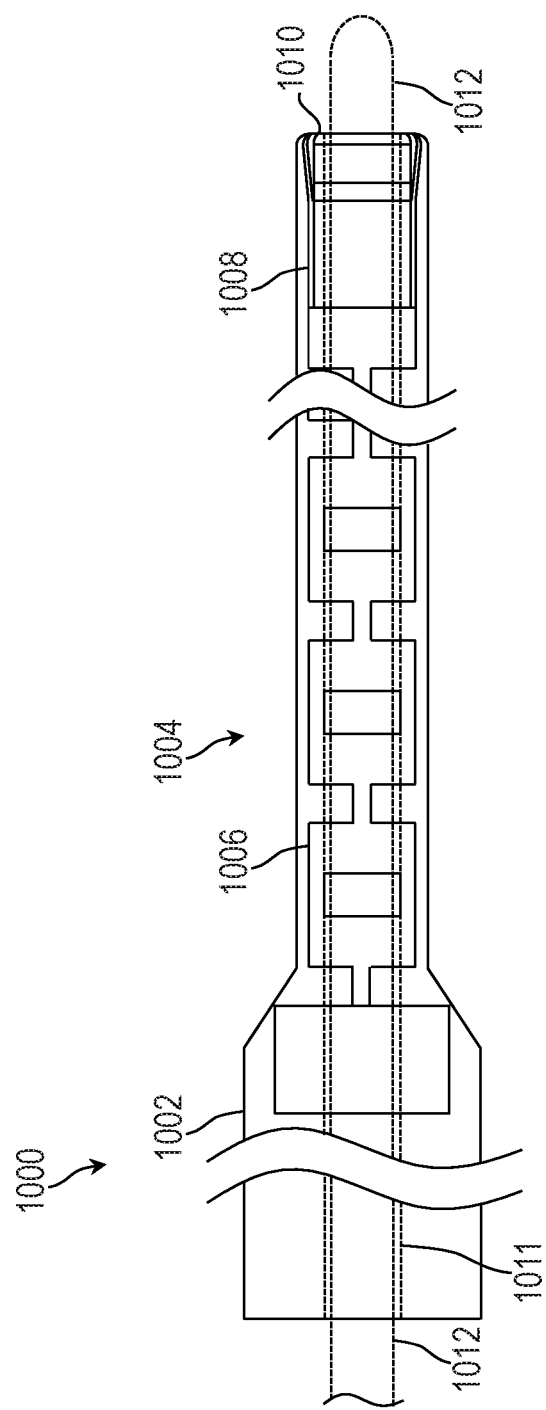
Figure 10B:
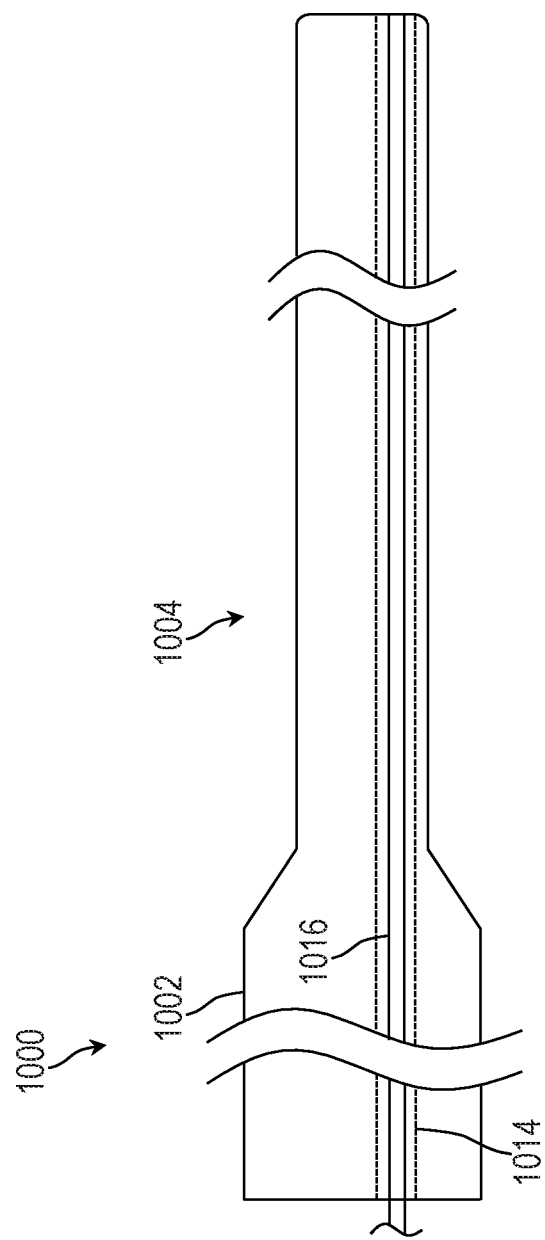

FIGS. 10A and 10B are side views of a medical instrument according to some embodiments of the present disclosure.

Figure 11:
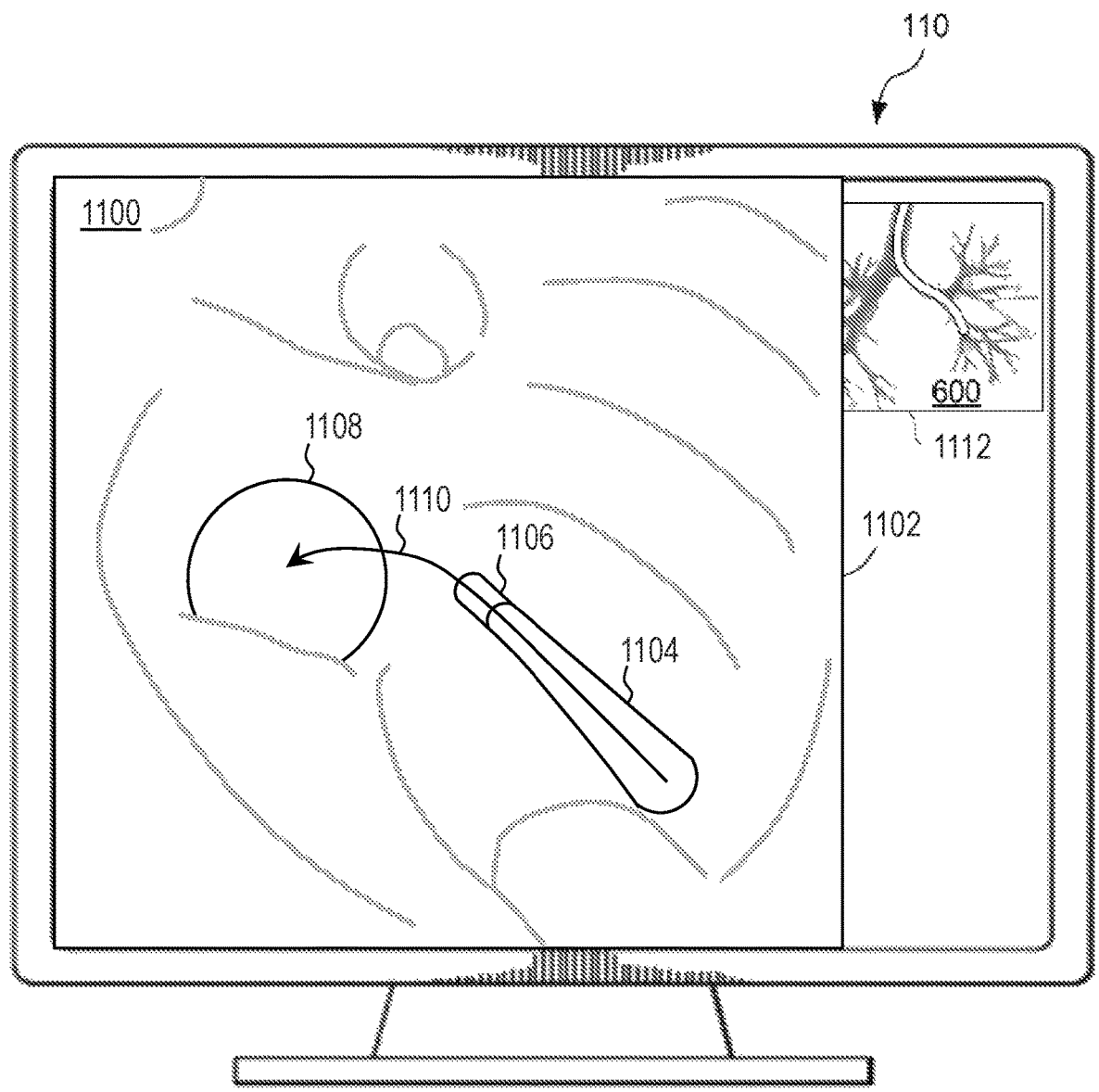

FIG. 11 illustrates a composite image that includes a representation of an updated preoperative model according to examples of the present disclosure.

Embodiments of the present disclosure are best understood from the following detailed description when read with the accompanying figures. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
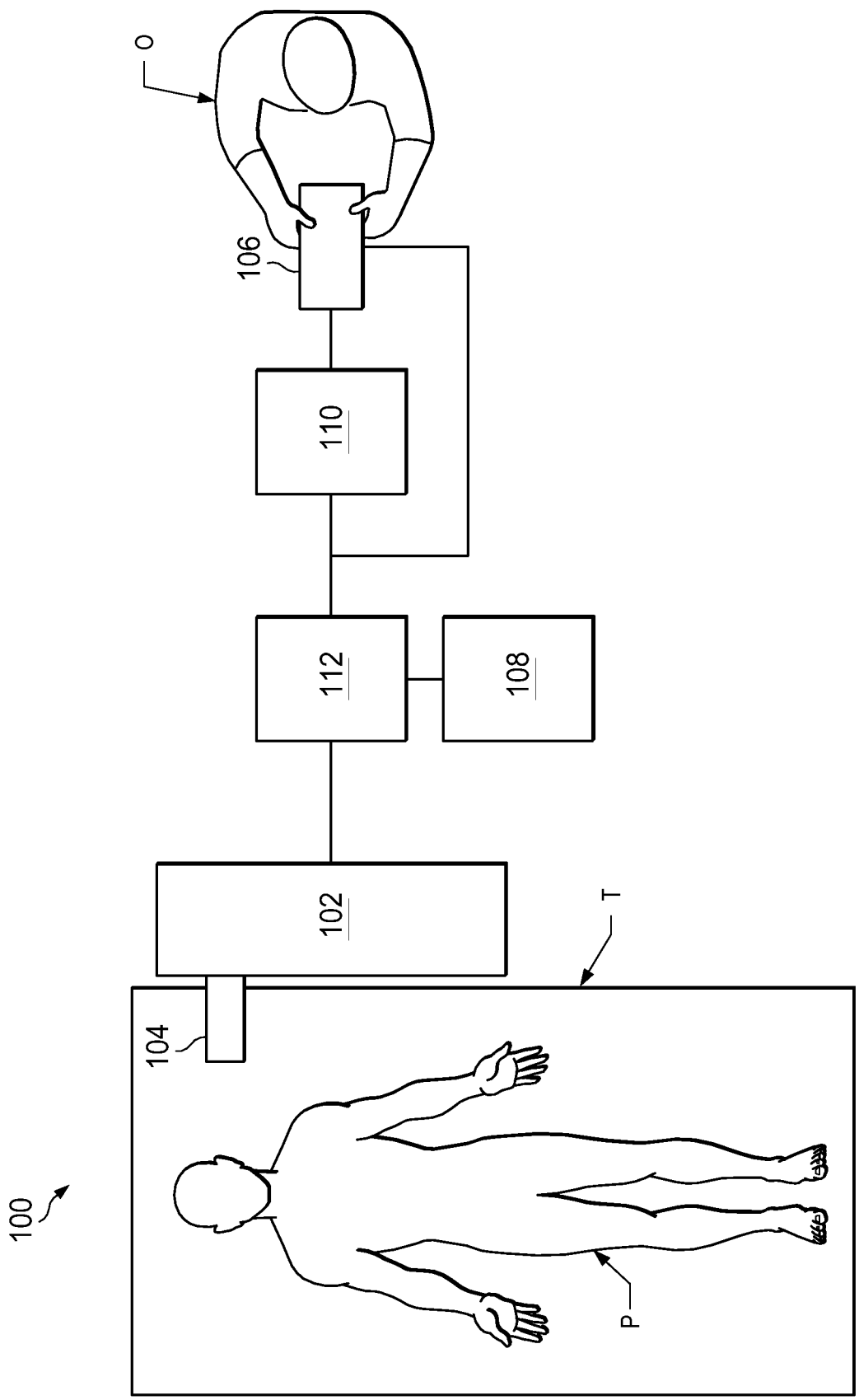
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a manipulator assembly 102 (which may be a teleoperated or partially teleoperated manipulator assembly) for operating a medical instrument 104 in performing various procedures on a patient P. Manipulator assembly 102 is mounted to or near an operating table T. A master assembly 106 allows an operator O (e.g., a surgeon, a clinician, or physician) to view the interventional site and to control the manipulator assembly 102.

Master assembly 106 may be located at a physician's console which is usually located in the same room as operating table T, such as at the side of a surgical table on which patient P is located. However, it should be understood that the operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide the operator O a strong sense of directly controlling the instrument 104, the control devices may be provided with the same degrees of freedom as the associated medical instrument 104. In this manner, the control devices provide operator O with telepresence or the perception that the control devices are integral with the medical instrument 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician who is physically manipulating medical instrument 104.

In some examples, display system 110 may present images of a surgical site recorded preoperatively or intraoperatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The preoperative or intraoperative image data may be presented as two-dimensional, three-dimensional, or four-dimensional (including e.g., time based or velocity based information) images and/or as images from models created from the preoperative or intraoperative image data sets.

In some embodiments, often for purposes of imaged guided medical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling the medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling the medical instrument 104 during an image-guided medical procedure. Virtual navigation using the virtual visualization system may be based upon reference to an acquired preoperative or intraoperative dataset of anatomic passageways. The virtual visualization system processes images of the surgical site imaged using imaging technology such as CT, MRI, fluoroscopy, thermography, ultrasound, OCT, thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intraoperatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/ expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the medical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202 coupled to a drive unit 204. Elongate device 202 includes a flexible body 216 having a proximal end 217 and a distal end 218. In some embodiments, flexible body 216 has an approximately 3 mm outer diameter. Other flexible body outer diameters may be larger or smaller. Examples of the elongate device 202 include endoscopes, bronchoscopes, catheters and other medical devices.

Medical instrument system 200 further includes a tracking system 230 for determining the position, orientation, speed, velocity, pose, and/or shape of the catheter tip at distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 m. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the catheter may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor including one or more conductive coils that may be subjected to an externally generated electromagnetic field. Each coil of the sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical tool 226. FIG. 2B is a simplified diagram of flexible body 216 with medical tool 226 extended according to some embodiments. In some embodiments, medical tool 226 may be used for procedures such as surgery, biopsy, ablation, illumination, irrigation, or suction. Medical tool 226 can be deployed through channel 221 of flexible body 216 and used at a target location within the anatomy. Medical tool 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical tool 226 is a biopsy instrument, which may be used to remove sample tissue or a sampling of cells from a target anatomic location. Medical tool 226 may be used with an image capture probe also within flexible body 216. In various embodiments, medical tool 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture probe may be a fiber-optic bundle, such as a fiberscope, that couples to visualization system 231. The image capture probe may be single or multi-spectral, for example capturing image data in one or more of the visible, infrared, and/or ultraviolet spectrums. Alternatively, medical tool 226 may itself be the image capture probe. Medical tool 226 may be advanced from the opening of channel 221 to perform the procedure and then retracted back into the channel when the procedure is complete. Medical tool 226 may be removed from proximal end 217 of flexible body 216 or from another optional instrument port (not shown) along flexible body 216.

Medical tool 226 may additionally house cables, linkages, or other actuation controls (not shown) that extend between its proximal and distal ends to controllably the bend distal end of medical tool 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 218. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator O or another operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

FIGS. 3A and 3B are simplified diagrams of side views of a patient coordinate space including a medical instrument mounted on an insertion assembly according to some embodiments. As shown in FIGS. 3A and 3B, a surgical environment 300 with a surgical environment reference frame $(X_s, Y_s, Z_s)$, in which a patient P is positioned on an operating table T. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a medical instrument 304 is coupled to an instrument carriage 306. In some embodiments, medical instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., manipulator assembly 102) that couples to medical instrument 304 to control insertion motion (i.e., motion along the A axis or in an $X_s$ direction) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Medical instrument 304 may be substantially similar to medical instrument system 200.

A three-dimensional imaging system 330 is arranged near the patient P to obtain three-dimensional images of the patient while the elongate device 310 is extended within the patient. The three-dimensional imaging system 330 may provide real-time or near real-time images of the patient P using imaging technology such as CT, fluoroscopy, thermography, ultrasound, OCT, thermal imaging, impedance imaging, laser imaging, nanotube X-ray imaging, and/or the like. In some embodiments, the imaging system 330 includes a mobile rotational imaging element such as that of a mobile C-arm cone-beam CT imaging system for capturing intraoperative 3D images and/or fluoroscopic 2D images. For example, the system 330 may be a DynaCT imaging system from Siemens Corporation of Washington, D.C., an Airo CT system from Brainlab AG of Munich, Germany, or other suitable imaging system. Accordingly, the imaging system 330 may capture a set of images, which may be still images, a series of still images, or video, from one or more angles by rotating the imaging element around the patient P. The images may be collected by the imaging system 330 while the elongate device 310 is positioned within patient P, and the images may include image information characterizing the elongate device 310 in physical relation to the anatomical structures of patient P. While referred to as a "three-dimensional" imaging system, the system 330 may capture two-dimensional, three-dimensional, or four-dimensional images.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear, while in other embodiments, the insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308, a component of the location of proximal point 316 along axis A may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero or another reference value. In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A.

FIGS. 4A, 4B, 4C, and 4D illustrate the advancement of the elongate device 310 of FIGS. 3A and 3B through anatomic passageways 402 of the lungs 400 of the patient P of FIGS. 1 and 3. These passageways 402 include the trachea and the bronchial airways. As the elongate device 310 is advanced as the carriage 306 moves along the insertion stage 308, the operator O may steer the distal end 318 of the elongate device 310 to navigate through the anatomic passageways 402. In navigating through the anatomic passageways 402, the elongate device 310 assumes a shape that may be measured by the shape sensor 314 extending within the elongate device 310. As noted above, when the imaging system 330 of FIGS. 3A and 3B captures images of the patient P when the elongate device 310 is positioned within the lungs 400 (or any other bodily structure or cavity), the elongate device 310 may appear in those images.

FIG. 5 is a flowchart illustrating a method 500 for performing image guided surgery in the surgical environment 300. The methods of this description, including method 500, are illustrated in FIG. 5 as a set of blocks, steps, operations, or processes. Not all of the illustrated, enumerated operations may be performed in all embodiments of the method 500. Additionally, some additional operations that are not expressly illustrated in the methods may be included before, after, in between, or as part of the enumerated processes. Some embodiments of the methods of this description include computer-readable instructions that corresponded to the processes of the methods as stored in a non-transitory memory. These instructions may be executed or coordinated by one or more hardware processors, like a processor of the control system 112.

Thus, some embodiments of the method 500 may begin at operation 502 in which intraoperative three-dimensional image data of a patient anatomy is obtained from an imaging system. The imaging system may be in use during an image-guided medical procedure. The image data may be obtained using imaging technology such as CT, MRI, thermography, ultrasound, OCT, thermal imaging, impedance imaging, laser imaging, or nanotube X-ray imaging. In some embodiments, the image data may include two-dimensional images from multiple perspectives that can be combined into pseudo-three-dimensional images. Thus, the intraoperative image data may correspond to two-dimensional, three-dimensional, or four-dimensional (including e.g., time based or velocity based information) images. In alternative embodiments, the image data may be acquired preoperatively and provide preoperative image data corresponding to two-dimensional, three-dimensional, or four-dimensional (including e.g., time based or velocity based information) images.

For example, the three-dimensional image data may include data representing at least a portion of a medical instrument 304 positioned within the anatomy of the patient P as shown in FIGS. 3A-B and 4A-D. This data may include a representation of the shape of the elongate device 310 of the medical instrument 304, and a three-dimensional model of the shape may be generated as part of the segmentation process. For example, the three-dimensional image data may be real-time or pseudo real-time image data obtained from an embodiment of the imaging system 330, such as a cone beam CT system.

At operation 504, as part of a registration process, pixels or voxels in the image data obtained in operation 502 that correspond to the medical instrument may be identified. To do so, in some embodiments, computer software, alone or in combination with manual input, is used to convert the intraoperative three-dimensional image data into one or more two-dimensional or three-dimensional composite representations or intraoperative models of the structures included in the image data. For example, the image data may be converted into an intraoperative model of a partial or an entire anatomic organ or anatomic region, like a torso including the lungs 400 of FIGS. 4A-D. The intraoperative model may describe the various locations and shapes of the anatomic passageways and their connectivity.

As the image data may also include an image of a medical instrument, such as the elongate device 310 as shown in FIGS. 4A-D, operation 504 may include a segmentation process to delineate sets of pixels or voxels representing specific structures, such as the elongate device 310 or another medical instrument or instruments. The operation 504 may then construct one or more models of the medical instrument(s). During the segmentation process, the pixels or voxels may be partitioned into segments or elements or be tagged to indicate that they share certain characteristics or computed properties such as color, density, intensity, and texture. The system performing the operation may then apply a function, such as a marching cube function, to generate a 3D surface that encloses the voxels. The model may be made by generating a mesh, volume, or voxel map. Additionally or alternatively, the surface-based model may include or may be used to generate a centerline model that includes a set of interconnected line segments or points extending through the center of the modeled instrument. Where the intraoperative model includes a centerline model including a set of interconnected line segments, those line segments may be converted to a cloud or set of points. By converting the line segments, a desired quantity of points corresponding to the interconnected line segments can be selected manually or automatically.

In some embodiments, the segmentation process may utilize shape information obtained from the elongate device 310 (obtained at operation 506 from the tracking system 230 or a similar operation). For example, a machine learning algorithm executing to process the image data may search the image data for a set of voxels having a shape that corresponding to a shape described by the shape information obtained from the elongate device 310 as described here. Voxels corresponding to the shape described by the shape information or a portion of the shape may be used to identify other voxels corresponding to the medical instrument having the shape. In some embodiments, the shape information may be used to identify a search region or search area that includes the voxels corresponding to the medical instrument. By using the shape information, the segmentation process employed to segment the medical instrument from the rest of the three-dimensional image data may be simplified and performed more rapidly. In this way, some embodiments of the operation 504 may include identifying a region of the three-dimensional image to segment using the shape data and segmenting the shape of the portion of the medical instrument from the region of the three-dimensional image.

For example, when a medical instrument like the medical instrument 200 or 304 is in place when CT images are obtained, the medical instrument or a portion thereof is included in the image. The medical instrument may be segmented or filtered out of the image and a model may be made of the medial instrument that includes a representation of the shape thereof. Similarly, anatomical passageways may be identified within the image data and used to general surface- or line-based models.

For example, the medical instrument 304 may be identified as a medical instrument in the image data by the segmentation or filtering by CT number or radiodensity value such as a Hounsfield value associated with the medical instrument 304 or a component thereof. This data associated with the medical instrument 304 may be isolated from other portions of the image data that are associated with the patient P or with specific tissue types. A three-dimensional mesh may be formed around the isolated data and/or a centerline may be determined that represents a centerline of the medical instrument.

In some embodiments, the three-dimensional mesh may be rendered in a display as a model. The model may be rendered opaquely or semi-transparently. One or more other models of anatomy may also be generated during a segmentation process. FIG. 6A depicts a rendered three-dimensional image 600, resulting from a three-dimensional CT image scan of human lungs. For example, the image 600 may be rendered to a display like the display 110 of FIG. 1. The image 600 is a filtered image that shows bronchial passageways 602 of the lungs and a flexible elongate medical instrument 604, which may be the elongate device 310 of the medical instrument 304 of FIGS. 3A and 3B, in some embodiments. As depicted in FIG. 6A, the image 600 has been segmented and filtered so that the soft tissues of the lungs are not visible. As seen in FIG. 6B, the image 600 may be segmented further so that only the medical instrument 604 is shown as a rendered model. The image data associated with the medical instrument 604 may be isolated and processed and manipulated separately from other types of the image data. The information in the image 600 corresponding to the medical instrument 604 may be segmented out and processed to generate a three-dimensional model of the shape of the medical instrument 604. FIGS. 6B depicts an isolated segmented shape model of the medical instrument 604 that corresponds to the shape information in the image 600.

As illustrated, the rendered image 600 further includes a target 606. For example, the target 606 may be a tumor or growth present in the lungs of the patient P. The three-dimensional image data may include data characterizing and defining a position and shape of the tumor, which can be segmented or filtered by the control system 112 to determine its position and shape and so that it can be selectively displayed. For example, the tumor may be rendered in image 600 as an opaque object, while other tissues are rendered to be semi-transparent, such that the tumor can been seen through other tissues. The control system 112 may calculate a position and orientation of the distal tip of the instrument 604 and may determine a vector 608 extending from the distal tip of the instrument 604 to the target 606. The vector 608 may be referred to as a trajectory vector and may indicate a direction in which the operator O should steer the medical instrument in order to access the target 606 for a biopsy or for treatment.

At operation 506, shape data or information may be obtained from the medical instrument while a portion of the medical instrument is positioned within the patient anatomy. In some embodiments, the operations 504 and 506 may be performed simultaneously or nearly simultaneously so that the information contained in the intraoperative three-dimensional image data and the shape data may have high correspondence in time. The shape data may be obtained by or from the tracking system 230, which interrogates or receives data from one or more sensors. For example, the tracking system 230 may receive position/shape information from an optical fiber shape sensor or other sensor system, such as a plurality of electromagnetic position sensors positioned along the elongate device 310. The sensor or sensors may be disposed at a known or tractable position in relation to physical features of the elongate device 310, like an outer tubular wall, that are visible in an acquired image or set of images including the medical instrument as positioned within the patient P. For example, the medical instrument 304 of FIGS. 3A and 3B includes an elongate device 310 having an optical fiber shape sensor 314 extending therein. As noted herein, the material of the elongate device 310 may be imaged by the imaging system 330 and be included in the three-dimensional image data characterizing the patient anatomy. The optical fiber shape sensor 314 may be used to obtain a collection of measured points that describe the shape of the elongate device 310 in terms of the instrument reference frame or shape sensor reference frame $(X_I, Y_I, Z_I)$. Accordingly, the shape data, as initially captured, may be expressed in the shape sensor reference frame, while the three-dimensional image, again as initially captured, is expressed in the image reference frame or anatomic model reference frame $(X_{CT}, Y_{CT}, Z_{CT})$.

At an operation 508, the segmented shape of the medical instrument may be registered with the shape data obtained from the medical instrument. In this way, the shape sensor reference frame or instrument reference frame $(X_I, Y_I, Z_I)$ is registered to the image reference frame or anatomic model reference frame $(X_{CT}, Y_{CT}, Z_{CT})$, or vice versa. This registration may rotate, translate, or otherwise manipulate by rigid or non-rigid transforms points associated with the segmented shape and points associated with the sensed shape data. This registration between the intraoperative model and instrument frames of reference may be achieved, for example, by using a point-based iterative closest point (ICP) technique as described in incorporated by reference U.S. Provisional Pat. App. Nos. 62/205,440 and No. 62/205,433, or another point cloud registration technique. Alternatively, registration may be performed by matching and registering feature points within instrument and image point clouds where point correspondences are determined from shape similarity in some feature space. In some embodiments, the segmented shape of the medical instrument is registered to the shape data in the shape sensor frame and the associated transform (a vector applied to each of the points in the segmented shape to align with the shape data in the shape sensor reference frame) may then be applied to the entire three-dimensional image and/or to subsequently obtained three-dimensional images during the medical procedure. The transform may be a six degrees-of-freedom (6DOF) transform, such that the shape data may be translated or rotated in any or all of X, Y, and Z and pitch, roll, and yaw.

In some embodiments, the shape sensor reference frame may be registered to the surgical environment reference frame $(X_S, Y_S, Z_S)$ or another patient reference frame, before the three-dimensional image is registered to the shape sensor reference frame. In this manner, both the shape data and the intraoperative three-dimensional image or model may be registered to a common reference frame, which may be the surgical environment reference frame. As the medical instrument may be coupled to an instrument carriage and/or an insertion stage at a known location within the surgical environment, the spatial relationship between the shape sensor reference frame and the surgical environment reference frame may be easily determined.

In some embodiments, a first transform may be applied to the three-dimensional image to bring that image into a shape sensor reference frame and a second transform may thereafter be applied to the three-dimensional image to bring it into the surgical environment reference frame. In some embodiments, these two transforms may be combined into a single transform. After the three-dimensional image and the shape data are co-registered, additional operations may be performed as part of operation 510, in which a medical procedure (such as surgery, biopsy, ablation, illumination, irrigation, or suction) is performed using the registered information to provide image-based guidance to the operator O by displaying registered information in a display.

Some embodiments of the method 500 may include operations that update the registration. For example, the control system 112 may detect or determine that the medical instrument positioned within the patient anatomy has been moved. Thereafter, an additional three-dimensional image of the patient anatomy may be captured. The registration may be updated based on the additional three-dimensional image. Additionally, some embodiments of the method 500 include obtaining a two-dimensional image of the patient anatomy while the portion of the medical instrument is positioned within the patient anatomy. This two-dimensional image may be obtained from the same perspective as the three-dimensional image, such that both images are obtained from a common imaging frame. Additionally, in some embodiments, the two-dimensional image may be obtained from a different imaging modality that is used to obtain the three-dimensional image. For example, the three-dimensional image may be a CT image, while the two-dimensional image is a fluoroscopic image. In some embodiments, the shape information may be used to register the three-dimensional image and the two-dimensional image to a common frame of reference.

Referring now to FIG. 7A, shown therein is a side view of the exemplary surgical environment 300 as discussed above in connection with FIGS. 3A and 3B. Compared with FIGS. 3A and 3B, the distal tip 318 of the elongate device 310 has been inserted deeper into the patient anatomy, such that a distal portion of the flexible elongate device 310 (shown in the area 700) takes on a shape that is at least partially dependent upon the anatomy to which the elongate device 310 is inserted. The shape of the distal portion in the area 700 is shown in greater detail in FIG. 7B, which also shows the optical fiber shape sensor 314 extending within the elongate device 310 to the distal tip 318. The shape sensor 314 may be interrogated to obtain shape data 710, depicted visually in FIG. 7C. This shape data corresponds to the shape of the elongate device 310 is positioned within patient anatomy. While the shape data 710 is visually depicted in FIG. 7C, the shape data 710 may be represented by numeric values, such as coordinates in the shape sensor reference frame, stored in memory. The shape data 710 and the three-dimensional image obtained by the imaging system 330 may include a timestamp to ensure that the information reflects the position and orientation of the medical instrument within the patient anatomy at approximately the same time period. The shape data 710 and the segmented shape of the model of the medical instrument 604 may be registered to bring the image data shown in image 600 into a common reference frame with the elongate device 310. This common reference frame may be the sensor or instrument reference frame $(X_I, Y_I, Z_I)$ or may be a reference frame of the surgical environment $(X_S, Y_S, Z_S)$. The instrument 304 and the imaging system 330 may both be included in embodiments of the medical system 100 of FIG. 1.

FIG. 8 depicts a composite image 800 produced from the registration of the segmented shape of the portion of the medical instrument with the shape data from the same portion of the medical instrument. This composite image 800 includes a surface model 802 of the bronchial passages, which are shown in an internal perspective of the anatomic passageways of the bronchial passageways 602 of FIG. 6. The surface model 802 may be generated from imaging data obtained using imaging technology as previously described. As shown in FIG. 8, an internal perspective may be provided to the operator O to facilitate image guided medical procedures. The internal perspective presents a view of the model 802 from the perspective of the distal tip of the medical instrument 804, which may be the same instrument shown as 604 in FIGS. 6A and 6B.

The composite image 800 further includes an image of a target 806. For example, the target 806 may be a tumor or growth present in the lungs of the patient P. The three-dimensional image data may include data characterizing and defining a position and shape of the tumor, which can be segmented or filtered so that its location can be determined and so that it can be selectively displayed. For example, the target 806 may be rendered as an opaque object, while other tissues are rendered to be semi-transparent, such that the tumor can been seen through other tissues. For example, when the target 806 is not co-located with a wall of the model 802, the model 802 may be rendered semi-transparently to permit a perspective view of the target 806. The control system 112 may calculate a position and orientation of the distal tip of the instrument model 804 and may determine a vector extending from the distal tip of the instrument model 804 to the target 806. The vector may be referred to as a trajectory vector 808 and may indicate a direction in which the operator O should steer the actual medical instrument in order to access the actual target for a biopsy or for treatment. The trajectory vector 808 may also be included in external perspective views, like that shown in FIG. 6A. FIG. 8 shows the composite image 800 rendered in a display, like the display 110 of FIG. 1. The control system 112 may cause other user interface elements to be displayed in display 110. For example, the display 110 also shows the image 600 of FIG. 6 in a window 810. As the operator O navigates within the patient, the perspectives shown in images 600 and 800 may update in real-time and be rendered to the display 110. Other information and elements may be presented in the display 110 to the operator O, such a physiological information or control elements.

The operator O may navigate within the patient anatomy, steering the medical instrument based on the image 600, which may include filtered CT image data. Because the medical instrument is registered to the image 600, movement of the medical instrument with respect to the patient P can be visualized by the display of corresponding movements of the displayed medical instrument 604, within the patient anatomy represented in the image 600.

In some embodiments, after the control system 112 determines and displays the trajectory vector 808, the control system 112 may impose constraints that override movement commands received from the operator O via the master assembly 106. For example, in some embodiments of the method 500, movement commands may be received from a user control device, like the master assembly 106, indicating a commanded movement of the distal tip of the medical instrument. The control system 112, or another component, may override the received movement commands to constrain movement of the distal tip of the medical instrument such that movement along the trajectory vector 808 is permitted while movement away from the trajectory vector 808 is not permitted. For example, the movement commands may be received as vectors indicating a direction in which the operator O desires to move the distal tip of the medical instrument. These movement command vectors may have components that are parallel to the trajectory vector 808 and components that are not parallel to the trajectory vector 808. The control system 112 may filter out the portion of the movement command vectors that are not parallel to the trajectory vector 808 and may cause the portion of the movement command vectors that are parallel to the trajectory vector 808 to be carried out by the servomotors.

In some embodiments, the trajectory vector 808 may be generated in response to a request from the operator O or based on a calculated distance from the target 806. Additionally, the operator O or another operator may be provided with a user interface element in the display 110, the selection of which permits the operator O to move the medical instrument away from the trajectory vector 808.

Further examples of a surgical method are described with reference to FIG. 9. In that regard, FIG. 9 is a flowchart illustrating a method 900 for performing image guided surgery in the surgical environment 300 according to some embodiments of the present disclosure. The methods of this description, including method 900, are illustrated in FIG. 9 as a set of blocks, steps, operations, or processes. Not all of the illustrated, enumerated operations may be performed in all embodiments of the method 900. Additionally, some additional operations that are not expressly illustrated in the methods may be included before, after, in between, or as part of the enumerated processes. Some embodiments of the methods of this description include computer-readable instructions that corresponded to the processes of the methods as stored in a non-transitory memory. These instructions may be executed or coordinated by one or more hardware processors, like a processor of the control system 112.

Referring to operation 902, preoperative image data of patient anatomy is obtained from an imaging system. In various examples, the image data includes CT data, MRI data, thermography data, ultrasound data, OCT data, thermal image data, impedance data, laser image data, nanotube X-ray image data, and/or other suitable data representing the patient anatomy. In some embodiments, the image data may include two-dimensional images from multiple perspectives that can be combined into pseudo-three-dimensional images. Thus, the preoperative image data may correspond to two-dimensional, three-dimensional, or four-dimensional (e.g., time based or velocity based information) images. The preoperative image data is in a first frame of reference (i.e., a preoperative image reference frame).

Referring to operation 904, a preoperative model of the patient anatomy is generated from the preoperative image data. As the model is generated from the preoperative image data, the preoperative model may be in the preoperative image reference frame. In some examples, distinguishing characteristics such as radiopacity, MRI response, density, and/or color are used to distinguish different tissues, structures, and voids within the patient anatomy. The model may contain part of or an entire anatomic organ or anatomic region, like a torso including the lungs 400 of FIGS. 4A-D. In one such example that models a lung, the model may describe the various locations and shapes of the anatomic passageways within the lung and their connectivity. In some examples, the model includes anatomic structures such blood vessels, lung pleura, large bullae, and/or the like.

Referring to optional operation 906 the operator can generate a navigation path through the anatomic passageways in the preoperative model to guide the medical instrument to a target. In that regard, the preoperative model may include a number of targets such as tumors, lesions, or other regions of tissue to be accessed during a medical procedure. Such medical procedures may include biopsy, ablation, illumination, irrigation, suction, etc. and may be performed by advancing a medical instrument (such as the medical instrument 304 of FIGS. 3A-B and 4A-D) through the anatomic passageways to the target. Accordingly, a planning step may be performed where the target is identified by the operator within the preoperative model and a navigation path is determined through the anatomic passageways of the preoperative model to guide the medical instrument to the target.

Referring to operation 908, the preoperative image reference frame is registered to the instrument reference frame. The medical instrument is advanced into the patient P, and specifically into the patient anatomy imaged in operation 902 and contained in the preoperative model of operation 904. This may be performed as part of a registration process or as a part of an image-guided medical procedure as described above. During the advancement, shape data in an instrument reference frame may be captured from sensors in the medical instrument. Since the medical instrument generally conforms to the passages of the anatomical structures of the patient's anatomy, the shape data obtained from the medical instrument corresponds to the location of the medical instrument in the patient. Accordingly, the computing system may determine the registration of the preoperative model's preoperative image reference frame to the medical instrument's instrument reference frame by comparing the shape data for the medical instrument to the shapes of the passages in the preoperative model.

Matching techniques such as ICP or Singular Value Decomposition (SVD) may be used to match the shape of the medical instrument to the shapes of the passages in the preoperative model. From this, the relationship between the medical instrument and the preoperative model is determined. Examples of this registration process are described in PCT Publication WO 2016/191298 (published Dec. 1, 2016) (disclosing "Systems and Methods of Registration for Image Guided Surgery"), which is herein incorporated by reference in its entirety.

In some examples, the medical instrument can be further advanced into the patient anatomy. In some examples, the medical instrument is advanced teleoperatively by the operator O along the navigation path of operation 906 towards the target. In alternative examples, the medical instrument may be advanced manually. In some examples the medical instrument is advanced with navigational guidance from the planned path generated from operation 906.

In some examples, the navigational guidance can be displayed in the preoperative model. A composite image, such as the composite image shown in FIG. 8, can be provided displaying a location of the instrument relative to the target and the anatomic passageways. As described in reference to FIG. 8, composite image 800 includes a surface model 802 of the bronchial passages, which are shown in an internal perspective of the anatomic passageways of the bronchial passageways 602 of FIG. 6. The surface model 802 may be generated from imaging data obtained using imaging technology as previously described. As shown in FIG. 8, an internal perspective may be provided to the operator O to facilitate image guided medical procedures. The internal perspective presents a view of the model 802 from the perspective of the distal tip of the medical instrument 804, which may be the same instrument shown as 604 in FIGS. 6A and 6B.

The composite image 800 further includes an image of a target 806. For example, the target 806 may be a tumor or growth present in the lungs of the patient P. The three-dimensional image data may include data characterizing and defining a position and shape of the tumor, which can be segmented or filtered so that its location can be determined and so that it can be selectively displayed. For example, the target 806 may be rendered as an opaque object, while other tissues are rendered to be semi-transparent, such that the tumor can been seen through other tissues. For example, when the target 806 is not co-located with a wall of the model 802, the model 802 may be rendered semi-transparently to permit a perspective view of the target 806. The control system 112 may cause other user interface elements to be displayed in display 110. For example, the display 110 also shows the image 600 of FIG. 6 in a window 810. As the operator O navigates within the patient, the perspectives shown in images 600 and 800 may update in real-time and be rendered to the display 110. Other information and elements may be presented in the display 110 to the operator O, such a physiological information or control elements.

The operator O may navigate within the patient anatomy, steering the medical instrument based on the image 600, which may include filtered CT image data. Because the medical instrument is registered to the image 600 and image 800, movement of the medical instrument with respect to the patient P can be visualized by the display of corresponding movements of the displayed medical instrument 604 and 804, within the patient anatomy represented in the image 600 and 800 respectively. In some examples (not shown), the medical instrument is positioned within the anatomic passageways at a distance from the target such that the target is not displayed in the model and an indicator providing directional guidance towards the target is displayed.

Referring to operation 910, intraoperative image data of the patient anatomy is obtained while the medical instrument is within the patient anatomy. In some examples, the medical instrument is proximate the target. Accordingly, the intraoperative image data may capture some combination of the patient anatomy, the medical instrument, and the target. Some aspects of operation 910 may be performed substantially as described in operation 502. An imaging system such as the three dimensional imaging system 330 above may obtain the intraoperative images using any suitable imaging technology such as CT, fluoroscopy, thermography, ultrasound, OCT, thermal imaging, impedance imaging, laser imaging, nanotube X-ray imaging, and/or the like. The imaging system may capture the set of intraoperative images, which may be still images, a series of still images, or video, from one or more angles by rotating the imaging element around the patient P. Accordingly, each intraoperative image may have a corresponding recorded time and orientation relative to the other images (e.g., angle of rotation).

Similarly, the intraoperative image data may have a corresponding orientation relative to the medical instrument. As the medical instrument moves in three dimensions, portions of the instrument may be indistinct or otherwise poorly imaged in some or all of the image data. For example a length of the instrument extending perpendicular to an imaging plane may not be properly captured in the intraoperative image data. Accordingly in some examples, a system (e.g., control system 112) directs the placement, shape, or orientation of the medical instrument prior to imaging in operation 910 to improve the imaging of the medical instrument. In one such example, the system directs the placement to increase the amount of the length of the medical instrument that is along an imaging plane. In another such example, the system directs the instrument to be bent or hooked along the imaging plane to create a distinct feature in the intraoperative image data. In some examples, a system (e.g., control system 112) directs the placement or orientation of the imaging system prior to imaging in operation 910 to improve the imaging of the medical instrument, for example to increase the amount of the length of the medical instrument that is along an imaging plane. The intraoperative image data as a whole may be in a second frame of reference (i.e., an intraoperative image reference frame) that is different from the preoperative image reference frame.

Referring to operation 912, the computing system registers the instrument reference frame to the intraoperative image reference frame. Some aspects of operation 912 may be performed substantially as described in operations 504-508. In some such examples, the computing system obtains shape data from the medical instrument that relates to the position, orientation, and/or pose of the medical instrument. A tracking system of the computing system may receive this position, orientation, and/or pose information from an optical fiber shape sensor or other sensor system, such as a plurality of electromagnetic position sensors positioned along an elongate device of the medical instrument. The sensor or sensors may be disposed at known or tractable positions in relation to physical features of the medical instrument, like an outer tubular wall, that are distinguishable in the intraoperative images. The sensors may be used to obtain a collection of measured points that describe the shape of the medical instrument within the instrument reference frame. This shape data may be obtained at regular intervals or in response to a trigger such as an interrupt or change in position of the medical instrument, and the shape data may include timestamps or other indicators of when each subset of the shape data was obtained. In an example, a subset of the shape data is obtained in response to an interrupt generated each time an imaging system captures an image of the intraoperative image data in operation 910.

The shape data may be used to help find the representation of the medical instrument in the image data. Accordingly, the computing system may perform segmentation of the image data to identify those portions of the intraoperative images that correspond to the medical instrument and those portions that correspond to the patient anatomy. By using the shape information, the segmentation process employed to segment the medical instrument from the rest of the three-dimensional image data may be simplified and performed more rapidly. Some aspects of segmentation may be performed substantially as described in operation 504. In some embodiments, a computing system converts the intraoperative image data into a two-dimensional or three-dimensional model of the patient anatomy, like a torso including the lungs 400 of FIGS. 4A-D, and a two-dimensional or three-dimensional model of the medical instrument. In various examples, pixels or voxels corresponding to the medical instrument are identified based in part on distinguishing characteristics visible in the intraoperative images such as radiopacity, MRI response, density, and/or color. For this purpose, the medical instrument may include structures detectable or visible within the intraoperative images that act as fiducial features.

For example, FIG. 10A and 10B are simplified diagrams of a side view of a medical instrument 1000 according to some embodiments of the present disclosure. The medical instrument 1000 includes an elongate device 1002, which may be substantially similar to elongate device 202 and/or elongate device 310. Referring to FIG. 10A, a distal portion 1004 of the elongate device 1002 contains an axial support structure 1006 that is configured to bend in response to actuation forces. Consequently, when unequal actuation forces are applied to the axial support structure 1006, the distal portion 1004 bends. Further examples of axial support structures are provided in U.S. patent application Ser. No. 15/685,979 (filed Aug. 24, 2017) (disclosing "Axial Support Structure for a Flexible Elongate Device") and U.S. Provisional Patent Application 62/535,673 (filed Jul. 21, 2017) (disclosing "Flexible Elongate Device Systems and Methods"), each of which is hereby incorporated by reference in its entirety. The axial support structure 1006 may have a characteristic in the intraoperative images (e.g., radiopacity, MRI response, density, and/or color) that distinguishes it from the surrounding patient anatomy and/or the remainder of the elongate device 1002. In further examples, the distal tip of the elongate device 1002 includes a control ring 1008, a tip ring 1010, or other structure at the distal tip with a distinguishing characteristic visible in the intraoperative images.

In some examples, the elongate device 1002 includes a tool lumen 1011. The tool lumen 1011 allows a medical tool 1012 be deployed through the elongate device 1002. The medical tool 1012 may be substantially similar to medical tool 226 above, and can be used for procedures such as surgery, biopsy, ablation, illumination, irrigation, or suction. Suitable medical tools 1012 include, biopsy instruments such as needles, laser ablation fibers, and/or other surgical, diagnostic, or therapeutic tools, and accordingly, the medical tool 1012 may have an end effector such as a scalpel, a blunt blade, forceps, graspers, scissors, clip appliers, and/or an electrode. The tool lumen 1011 and parts of the medical tool 1012 such as the end effector may have a distinguishing characteristic in the intraoperative images and may thereby act as a fiducial feature.

Referring to FIG. 10B, the elongate device 1002 may also include a shape sensor lumen 1014 through which a shape sensor 1016 extends. The shape sensor 1016 may be substantially similar to shape sensor 222 above and may include an optical fiber extending through the shape sensor lumen 1014. To reduce discrepancies between data obtained via the shape sensor 1016 and the imaging data, the shape sensor lumen 1014 and/or the shape sensor 1016 may have a distinguishing characteristic in the intraoperative images in order to act as a fiducial feature. As the shape sensor lumen 1014 may be in close proximity to the shape sensor 1016 disposed therein, the imaging data corresponding to the shape sensor lumen 1014 may closely track the shape data obtained from the shape sensor 1016.

Referring back to operation 912 of FIG. 9, the computing system performing segmentation identifies these fiducial features (e.g., the axial support structure 1006, the control ring 1008, the tip ring 1010, the tool lumen 1011, the medical tool 1012, the shape sensor lumen 1014, the shape sensor 1016) in the intraoperative image data to identify one or more portions of the medical instrument and uses the position, orientation, and/or pose of the medical instrument determined from the shape data obtained above to register the instrument reference frame to the intraoperative image reference frame. The registration may rotate, translate, or otherwise manipulate by rigid or non-rigid transforms points associated with the segmented shape and points associated with the sensed shape data. This registration between the instrument and intraoperative image frames of reference may be achieved, for example, by using an ICP technique or another point cloud registration technique. Alternatively, registration may be performed by matching and registering feature points within instrument and image point clouds where point correspondences are determined from shape similarity in some feature space. In some embodiments, the segmented shape of the medical instrument is registered to the shape data in the shape sensor frame and the associated transform (a vector applied to each of the points in the segmented shape to align with the shape data in the instrument reference frame) may then be applied to the entire three-dimensional image and/or to subsequently obtained three-dimensional images during the medical procedure. The transform may be a 6DOF transform, such that the shape data may be translated or rotated in any or all of X, Y, and Z and pitch, roll, and yaw.

To improve the accuracy of this process, the computing system may optionally perform a temporal match of the shape data to the intraoperative image data. In some examples, the shape data includes multiple subsets each containing data points taken at discrete times. The subsets may be obtained at regular intervals or in response to a trigger such as an interrupt or change in position of the medical instrument, and the shape data may include timestamps or other indicators of when each unit of shape data was obtained. Similarly, the images that make up the intraoperative image data may each have a timestamp recording when the image was obtained. In such examples, the computing system performing registration may utilize the timestamps to correlate a subset of the shape data with an image of the intraoperative image data in time. In that regard, the computing system may determine the registration of the instrument reference frame to the intraoperative image reference frame by comparing an intraoperative image obtained at a point in time with the contemporaneous subset of the shape data. This may reduce errors caused by anatomical movement, instrument movement, or sensor drift over time.

Additionally or in the alternative, the computing system may optionally correlate the timing of the shape data and the images to a cyclic motion. For example, the patient anatomy may move during regular cyclic activity (e.g., cardiac activity, respiratory activity, etc.). The computing system may determine at what stage (e.g., diastole phase, respiratory hold) of the cyclic activity each subset of the shape data and each image of the intraoperative image data was obtained. To do so, timestamps or triggers associated with the data may be correlated with various other patient status monitors, such as a cardiac monitor or respiratory monitor (e.g., a patient pad), that monitor the cyclic activity. Accordingly, the computing system may determine the registration of the instrument reference frame to the intraoperative image reference frame by comparing an intraoperative image obtained at a particular stage of a cyclic activity with a subset of the shape data obtained at the same stage. As the activity may be periodic, image data from one cycle of the activity may be compared with a subset of the shape data obtained during another cycle. Furthermore, some points during a cyclic activity may be more conducive to imaging. Accordingly in some examples, an intraoperative image taken during an optimal point during the cyclic activity is identified and compared with a subset of the shape data obtained concurrently.

As the intraoperative image data may not capture the entirety of the medical instrument, in some examples, the computing system optionally divides the medical instrument into portions and determines those portions that were captured by each image of the intraoperative image data. For each imaged portion, the computing system may correlate the shape data for the portion with the image of the intraoperative image data. This may include temporal as well as spatial correspondence. For example, if a first image of the intraoperative image data captured the most distal portion of the medical instrument in the first second of scanning, the shape data for the most distal portion corresponding to the first second of scanning may be compared to the first image. If a second image of the intraoperative image data captured the second-most distal portion of the medical instrument in the second second of scanning, the shape data for the second-most distal portion corresponding to the second second of scanning may be compared to the second image.

To further improve accuracy, the computing system may make multiple comparisons and may weight each comparison individually. As noted above, the intraoperative image data may include a set of images taken at different orientations. For example, intraoperative image data obtained by a mobile rotational imaging element may include a set of images, each with a different time, location, and rotational orientation relative to the patient P. The computing system may perform registration using some or all of the images in the data set. In that regard, each image may be given a weight based on its point in time (absolute time or time relative to a cyclic activity), location, orientation, and/or other factors. For example, an image may be obtained during a point in time with significant patient movement and may be weighted less than other images in the set. In another example, an image taken at an orientation where the medical instrument, the target, or another anatomic structure is less visible may be weighted less. In another example, an image may be of low quality and may be weighted less. The computing system may consider the weighting factor associated with each image or each unit of shape data when determining the registration of the instrument reference frame to the intraoperative image reference frame. In some embodiments, suboptimal images may be identified and retaken by repeating operation 910. Registration may then be performed using the retaken intraoperative images.

Referring next to operation 914, the preoperative image reference frame of the preoperative model is registered to the intraoperative image reference frame. As described above, the computing system may register the preoperative image reference frame to the instrument reference frame in operation 908 and register the instrument reference frame to the intraoperative image reference frame in operation 912. Accordingly, registration of the preoperative image reference frame to the intraoperative image reference frame may be performed using the common frame of reference (i.e., the instrument reference frame).

Additionally or in the alternative, the preoperative reference frame may be registered to the intraoperative reference frame using feature-based registration to compare the respective models and/or images, and the computing system locates corresponding fiducial features in the intraoperative model/images and the preoperative model/images. Fiducial features include both artificial and anatomical features with a distinguishing characteristic (e.g., radiopacity, Mill response, density, and/or color) in the intraoperative image data, preoperative image data, and/or preoperative model. The distinguishing characteristic may be different in each dataset, for example, Mill response in preoperative Mill data and radiopacity in the intraoperative image data. Suitable fiducial features include bone, tissue boundaries, other organs and organ systems, voids, and artificial features inside and outside the anatomy. In some examples, a set of external fiducial feature such as a patient pad or a stereotactic frame is placed on the patient during the preoperative and intraoperative imaging. Once corresponding fiducial features are identified in the intraoperative image data and some combination of the preoperative image data and/or the preoperative model, the positions and orientations of the fiducial feature may be used to determine a relationship between the preoperative image reference frame and the intraoperative image reference frame.

As a supplement to or alternative to, feature-based registration, the computing system may perform image-based matching to match individual images from the preoperative image data or model to images from the intraoperative image data. For a given preoperative image, the computing system may select a corresponding intraoperative image for comparison or vice-versa. The corresponding images may be selected based on their locations, orientations, and/or other factors. In an example where the intraoperative image data is obtained by a mobile rotational imaging element, each intraoperative image may have a location and a rotational orientation relative to the patient P. For some or all of the intraoperative images, corresponding preoperative image may be selected based on having a similar location and rotational orientation to the patient P. If such a preoperative image is not available, one may be generated by simulating an image taken at the location and rotational orientation using the preoperative model.

The computing system may optionally perform a temporal match of the preoperative image data or model to the intraoperative image data. In some such examples, the preoperative image data or model and the intraoperative image data may include timestamps indicating when each image was obtained. In some such examples, corresponding images may be selected based on these timestamps. The timestamps may be correlated with various other patient status monitors to monitor a cyclic activity and determine at what stage during the cyclic activity the image was taken. For an intraoperative image taken at a particular phase (e.g., diastole phase, respiratory hold) during the cyclic activity, a corresponding preoperative image may be selected based on being taken at a similar or corresponding phase of the activity.

Once corresponding images have been selected, they may be compared to determine variations in position and/or orientation and thereby determine a relationship between the preoperative image reference frame and the intraoperative image reference frame.

In some examples, each image or pair of corresponding images may be given a weight based on their point in time (absolute time or time relative to a cyclic activity), location, orientation, and/or other factors. For example, an image may be obtained during a point in time with significant patient movement and may be weighted less than other images. In another example, an image taken at an orientation where a fiducial feature is less visible may be weighted less. In another example, an image may be of low quality and may be weighted less. The computing system may consider the weighting factor associated with each image when determining the registration of the preoperative image reference frame to the intraoperative image reference frame. In some embodiments, suboptimal intraoperative images may be identified and retaken by repeating operation 910.

It is noted that shape-based registration may be combined with feature-based and/or image-based registration by iterating the two registration processes one or more times, with each iteration increasing the accuracy of the registration of the preoperative image reference frame to the intraoperative image reference frame.

With the two image reference frames registered, the computing system may update the preoperative model based on the intraoperative image data as illustrated in operation 916. Referring back to FIG. 8 as an example, the preoperative model includes a patient anatomy, a target such as a tumor or other region of tissue to be treated, and/or a representation of a medical instrument. After capturing an intraoperative image, the real-time location of the tumor relative to other anatomical structures and/or the instrument may have shifted from a location represented in the preoperative model as shown in FIG. 8 The computing system may update a size, a location, and/or another property of the target based on the intraoperative image data. In one such example, the computing system updates a location of the target based on a distance measured between the medical instrument and the corresponding tissue determined from the intraoperative image data and/or the shape data obtained from the medical instrument. If the preoperative model varies from the intraoperative image data by more than a threshold, some or all of the preoperative model may be replaced to reflect the real time location of the tumor relative to medical instrument. In an alternative example, the computing system generates a new model from the intraoperative image data substantially as described in operation 904 when the preoperative model varies more than the threshold and the intraoperative model is used to replace some or all of the preoperative model. In some examples, other anatomical structures such as passageways, blood vessels, and the like are provided in the preoperative model generated in operation 904. In such examples, the size, shape, and/or relative location of the other anatomical structures may also up updated in the preoperative model in a similar manner. In this manner, anatomical structures which should be avoided can be displayed as further navigational aids during a medical procedure.

Referring to operation 918, optionally, the computing system may display a representation of the preoperative model as updated in operation 916. FIG. 11 depicts a composite image 1100 that includes a representation of the preoperative model according to examples of the present disclosure displayed on a display 110 such as that of FIG. 1. Image 1100 may be substantially similar to image 800 in many regards. The composite image 1100 includes a surface model 1102 of a passageway (e.g., a bronchial passage) in which the medical instrument is located generated from the preoperative model. An internal perspective may be provided to the operator O to facilitate image guided medical procedures. The internal perspective presents a view of the model 1102 from the perspective of the distal tip of the medical instrument. For reference, a rendering 1104 of the medical instrument may be displayed. If a medical tool has been extended through the medical instrument, a rendering 1106 of the medical tool may be displayed.

The composite image 1100 further includes an image of the target 1108. The target 1108 may be rendered as an opaque object, while other tissues are rendered to be semi-transparent, such that the tumor can been seen through other tissues. For example, when the target 1108 is not co-located with a wall of the model 1102, the model 1102 may be rendered semi-transparently to permit a perspective view of the target 1108. The computing system may calculate a position and orientation of the distal tip of the instrument model 1104 and may display a trajectory vector 1110 extending from the distal tip of the instrument model 1104 to the target 1108. Other information and elements may be presented in the display 110 to the operator O, such a physiological information or control elements. For example, the display 110 may include the image 600 of FIG. 6 in a window 1112.

Optionally, the operator O and/or teleoperational system may use the updated preoperative model to perform an image-guided medical procedure. For example, the operator O or teleoperational system may navigate the medical instrument within the patient anatomy by steering the medical instrument based on the image 1100. Because the medical instrument is registered to the image 1100, movement of the medical instrument with respect to the patient P can be visualized by displaying corresponding movements of the displayed medical instrument 1104 within the patient anatomy represented in the image 1100. Once the medical instrument is positioned near the target, the operator O may advance a medical tool, such as the medical tool 226 of FIG. 2, through the medical instrument. The operator O may use the medical tool to perform a procedure such as surgery, biopsy, ablation, illumination, irrigation, or suction on the target, and may visualize the movement and operation of the medical tool using the rendering 1106 thereof during the procedure.

Referring to operation 920, optionally, a second set of intraoperative images may be obtained. This may be performed substantially as described in operation 910. The second set of intraoperative images may be used to assess the efficacy of the procedure. In an example, the operator O performs an ablation procedure on the target, and the second set of intraoperative images captures the target and surrounding anatomy to assess the effect of the ablation procedure on the target. In some examples, patient movement may cause a shift in anatomy, target, and/instrument location. Accordingly, the registration techniques described can be used to register the second set of intraoperative images to a first set of intraoperative images taken prior to the ablation procedure or to register the second set of intraoperative images to the preoperative model.

In some examples, obtaining the second set of intraoperative images includes determining a localized region to image based on the registration of the instrument reference frame to the intraoperative reference frame of operation 912. As the position of the medical instrument and the target in the intraoperative reference frame is known, the region to image may be determined more precisely. Obtaining the second set of intraoperative images using a relatively smaller region may reduce patient exposure to radiation. In some examples, the second set of intraoperative images can be taken to supplement low quality images in a first set of intraoperative images. In some examples, a plurality of intraoperative images may be taken, each of which may be registered to the preoperative model or any prior intraoperative image.

Some of these embodiments of the present disclosure may facilitate registration of a three-dimensional image or a set or series of three-dimensional images with the shape of a medical instrument. For example, an image or images from a cone-beam CT scanner that are obtained while a medical instrument is in place can be registered to the medical instrument by also obtaining shape data from that medical instrument at or around the time the image or images are captured. A transform relating the shape of the medical instrument in an image to shape data from an optical fiber shape sensor can be applied to the entire image, or a portion thereof, to bring the image into a common reference frame with the medical instrument. Additionally, images such as preoperative images, may also be registered into the common reference frame for use in image-guided medical procedures. Furthermore, the location of a tumor or other target in the image may be used to constrain or otherwise modulate movement commands received from an operator so that the medical instrument follows a determined trajectory to the tumor for a biopsy or treatment.

One or more elements in embodiments of the invention may be implemented in software to execute on a processing device of a computer system such as control system 112. When implemented in software, the elements of the embodiments of the invention are essentially the code segments to perform the necessary tasks. The program or code segments can be stored in a non-transitory machine-readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein. Additionally, features described in more detail with respect to a particular embodiment may be combined with features of other embodiments.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method performed by a computing system, the method comprising:
   obtaining a three-dimensional image of a patient anatomy and a portion of a medical instrument disposed therein, the three-dimensional image including image information characterizing a shape of the portion of the medical instrument;
   obtaining shape data from the portion of the medical instrument while the portion is positioned within the patient anatomy;
   based on the shape data, identifying a region of the three-dimensional image to segment while the medical instrument is positioned within an anatomical passageway of the patient anatomy;
   segmenting, by a processing device, the portion of the medical instrument from the region of the three-dimensional image, wherein the segmenting includes:
      isolating image data associated with the portion of the medical instrument from other image data associated with the patient anatomy; and
      augmenting the isolated image data associated with the portion of the medical instrument; and
   registering, by the processing device, the segmented portion of the medical instrument from the three-dimensional image with the shape data from the portion of the medical instrument.

2. The method of claim 1, further comprising:
   displaying the three-dimensional image on a display;
   displaying a representation of the medical instrument on the display; and
   receiving a movement command from an operator based on the display of the three-dimensional image and the representation of the medical instrument.

3. The method of claim 1, further comprising:
   determining a position and orientation of a distal tip of the medical instrument;
   identifying a target location for the distal tip of the medical instrument; and
   generating a trajectory vector pointing to the target location, the trajectory vector based on the position and orientation of the distal tip of the medical instrument.

4. The method of claim 1, further comprising:
   receiving a preoperative model of the patient anatomy, wherein the preoperative model is in a preoperative reference frame; and
   registering the preoperative reference frame to an image reference frame of the three-dimensional image.

5. The method of claim 4, further comprising registering the preoperative reference frame to an instrument reference frame of the medical instrument, wherein the shape data from the portion of the medical instrument is in the instrument reference frame.

6. A medical system comprising:
   a medical instrument comprising a shape sensor;
   a tracking subsystem configured to receive shape data from the shape sensor; and
   a processor coupled to the medical instrument and the tracking subsystem, the processor being configured to:
      receive image data of a patient anatomy that has the medical instrument disposed therein, wherein the image data is in an image reference frame;
      obtain the shape data from the medical instrument while the medical instrument is positioned within the patient anatomy, wherein the shape data is in an instrument reference frame;
      based on the shape data, identify a subset of the image data to segment while the medical instrument is positioned within an anatomical passageway of the patient anatomy;
      segment the subset of the image data corresponding to the medical instrument by:
         isolating image data associated with the medical instrument from other image data associated with the patient anatomy; and
         augmenting the isolated image data associated with the medical instrument; and
      register the instrument reference frame to the image reference frame by comparing the shape data to the subset of the image data corresponding to the medical instrument.

7. The medical system of claim 6, wherein the image data includes a three-dimensional CT image.

8. The medical system of claim 6, wherein the shape sensor is an optical fiber shape sensor extending through at least a portion of the medical instrument and terminating at a proximal point.

9. The medical system of claim 6, wherein the processor is further configured to:
   receive a preoperative model of the patient anatomy, wherein the preoperative model is in a preoperative reference frame; and
   register the preoperative reference frame to the image reference frame.

10. The medical system of claim 9, wherein the processor is further configured to register the preoperative reference frame to the instrument reference frame.

11. The medical system of claim 10, wherein the registration of the preoperative reference frame to the image reference frame is based on the registration of the preoperative reference frame to the instrument reference frame and the registration of the instrument reference frame to the image reference frame.

12. The medical system of claim 11, wherein the registration of the preoperative reference frame to the image reference frame is further based on at least one of a feature-based registration of the preoperative reference frame to the image reference frame and an image based registration of the preoperative reference frame to the image reference frame.

13. The medical system of claim 12, wherein the feature-based registration includes comparing a fiducial feature of the preoperative model to a fiducial feature of the image data.

14. The medical system of claim 13, wherein the fiducial feature of the preoperative model and the fiducial feature of the image data each correspond to at least one of an anatomical structure or an artificial structure.

15. The medical system of claim 14, wherein the processor is further configured to:
provide a representation of the preoperative model of the patient anatomy for display; and
provide a representation of the medical instrument within the preoperative model for display.

16. The medical system of claim 15, wherein the processor is further configured to update the preoperative model based on the image data.

17. The medical system of claim 6, further comprising at least one fiducial element, wherein the at least one fiducial element includes at least one of a medical instrument support structure, a medical instrument control ring, a medical instrument tip ring, a medical instrument lumen, or a medical tool extending through the medical instrument.

18. The medical system of claim 17, wherein segmenting the subset of the image data corresponding to the medical instrument includes identifying the at least one fiducial element.

19. The medical system of claim 6, wherein the processor is further configured to:
determine that the medical instrument has moved;
obtain additional image data of the patient anatomy; and
update the registration of the instrument reference frame to the image reference frame based on the additional image data.

20. The medical system of claim 6, wherein the processor is further configured to:
determine a position and orientation of a distal tip of the medical instrument;
identify a target location for the distal tip of the medical instrument; and
generate a trajectory vector pointing to the target location based on the position and orientation of the distal tip of the medical instrument.

* * * * *

UNITED STATES PATENT AND TRADEMARK OFFICE
CERTIFICATE OF CORRECTION

PATENT NO. : 11,779,396 B2
APPLICATION NO. : 16/473439
DATED : October 10, 2023
INVENTOR(S) : Vincent Duindam et al.

Page 1 of 1

It is certified that error appears in the above-identified patent and that said Letters Patent is hereby corrected as shown below:

In the Specification

Column 25, Line 52, change "Mill" to -- MRI --

Column 25, Line 56, change "Mill response" to -- MRI response --

Column 25, Line 56, change "Mill data" to -- MRI data --

Signed and Sealed this
Fifth Day of December, 2023

Katherine Kelly Vidal
*Director of the United States Patent and Trademark Office*